(12) United States Patent
Lee et al.

(10) Patent No.: US 9,494,523 B2
(45) Date of Patent: Nov. 15, 2016

(54) METHOD FOR VERIFYING REPRESENTATIVENESS OF SAMPLE COLLECTED IN CONTAMINATED SOIL

(75) Inventors: Pyeong-Koo Lee, Daejeon (KR); Seung-Jun Youm, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 1157 days.

(21) Appl. No.: 13/300,367

(22) Filed: Nov. 18, 2011

(65) Prior Publication Data

US 2012/0154802 A1   Jun. 21, 2012

(30) Foreign Application Priority Data

Dec. 17, 2010   (KR) .................. 10-2010-0129722

(51) Int. Cl.
*G01N 21/73*   (2006.01)
(52) U.S. Cl.
CPC ..................... *G01N 21/73* (2013.01)
(58) Field of Classification Search
CPC ...... B09C 1/08; G01N 33/24; G01N 1/2294; G01N 21/73
USPC .......... 702/2, 22, 23, 30, 179, 181
See application file for complete search history.

(56) References Cited

U.S. PATENT DOCUMENTS

| 4,809,790 | A | 3/1989 | Manchak, Jr. |
| 6,591,702 | B2 * | 7/2003 | Hayes et al. .......... 73/866 |
| 2004/0223811 | A1 * | 11/2004 | Bruso .......... 405/128.75 |

FOREIGN PATENT DOCUMENTS

KR   10-1999-0061772   7/1999

OTHER PUBLICATIONS

Cheng et al., Background Concentrations of Trace Metals in Florida Surface Soils: Taxonomic and Geographic Distributionsof Total-total and Total-recoverable Concentrations of Selected Trace Metals, Dec. 1999, pp. xvi-xviii, and 1-1 to 5-27.*
Gilbert, Statistical Methods for Environmental Pollution Monitoring, 1987, Van Nosstrand Reinhold Company, pp. 1-320.*
Lee, Jong-Pyo, *Characteristics of Potentially Toxic Heavy Metals at Dukun Area*, Dept. of Mineral Resource Engineering, Graduate School, Chosun University, (1997), 106 pages, English Abstract (pp. IX and X).

* cited by examiner

*Primary Examiner* — Manuel L Barbee
*Assistant Examiner* — Yaritza H Perez Bermudez
(74) *Attorney, Agent, or Firm* — Lewis Roca Rothgerber Christie LLP

(57) ABSTRACT

Disclosed is a method for verifying representativeness of samples collected in a contaminated soil. The method includes the steps of horizontally and vertically collecting the samples from the contaminated soil on a basis of a stratum of the contaminated soil at a predetermined sampling interval; measuring a total concentration of trace elements by analyzing the collected samples according to the sampling interval; and determining horizontal and vertical sampling intervals and a sample number based on a statistical analysis result for the total concentration of the trace elements.

8 Claims, 16 Drawing Sheets

METHOD FOR VERIFYING REPRESENTATIVENESS OF SAMPLE COLLECTED IN CONTAMINATED SOIL

CROSS-REFERENCE TO RELATED APPLICATION

This application claims the benefit under 35 U.S.A. §119 of Korean Patent Application No. 10-2010-0129722, filed on Dec. 17, 2010 in the Korean Intellectual Property Office, the entirety of which is incorporated herein by reference.

BACKGROUND OF THE INVENTION

1. Field of the Invention

The embodiments of the present invention relate to a method for verifying representativeness of a sample collected in a contaminated soil.

2. Description of the Related Art

The sampling method according to the current standard for the environmental pollution test is as follows.

Although the soil sampling is a simple work, the soil is not uniformly distributed in the vertical and horizontal directions, so the soil sample must be carefully collected because the collected sample stands for the target region. The sampling error is always greater than the analysis and measurement error, so the soil sample must be carefully and accurately collected.

In the case of the farm land, five to ten points are selected in a zigzag manner from the target region. In the case of other regions, such as a factory region, a reclamation region and a street region, five points are selected, in which one point serves as the center of the target region and four points are located at four corners around the one point within 5 to 10 m. If the distance between adjacent points is insufficient due to facilities installed in the target region, the distance can be appropriately adjusted.

However, a method for determining the number of samples to be collected based on the area and depth of the soil contamination survey region and a method for verifying the representativeness of the collected sample have not been suggested yet. Thus, a surveyor determines the number of samples to be collected according to the survey purpose, so serious problems raise in relation to the representativeness of the collected sample.

Therefore, it is necessary to develop a method for determining the number of samples to be collected and verifying the representativeness of the collected sample when the sample is collected vertically and horizontally in the contaminated soil.

SUMMARY OF THE INVENTION

According to one embodiment of the present invention, there is provided a method for determining the number of samples to be collected and verifying the representativeness of the collected sample when the sample is collected vertically and horizontally in the contaminated soil.

According to one embodiment of the present invention, there is provided a method for verifying the representativeness of a sample collected in a contaminated soil, in which samples are collected at regular intervals according to the horizontal level (stratum) and the depth thereof from tailings of a single mine and then the statistical analysis is performed with respect to the concentration of the trace elements in the tailings to determine the horizontal/vertical sampling intervals and the number of the samples standing for the tailings, thereby standardizing the sampling method.

The object of the present invention is not limited to the above, and other objects, which are not described, can be clearly comprehended from the following description by those skilled in the art.

According to one aspect of the present invention, there is provided a method for verifying representativeness of samples collected in a contaminated soil, in which the method includes the steps of horizontally and vertically collecting the samples from the contaminated soil on a basis of a stratum of the contaminated soil at a predetermined sampling interval; measuring a total concentration of trace elements by analyzing the collected samples according to the sampling interval; and determining horizontal and vertical sampling intervals and a sample number based on a statistical analysis result for the total concentration of the trace elements.

The step of horizontal collecting the samples includes the step of regularly setting the sampling intervals and gradually widening the sampling intervals in a horizontal direction by a predetermined distance.

The step of vertical collecting the samples includes the step of regularly setting the sampling intervals and gradually widening the sampling intervals in a vertical direction by a predetermined distance.

The total concentration of the trace elements is measured through a pretreatment by using aqua regia and a chemical analysis by using inductively coupled plasma-atomic emission spectroscopy (ICP-AES).

The statistical analysis for the total concentration of the trace elements includes the steps of sub-dividing all samples into sub-groups; and comparing whether an average concentration of trace elements in each sub-group is identical to an average concentration of trace elements in all samples.

The sub-groups include samples selected by taking the sampling interval into consideration in a case of horizontally collected samples, and include samples selected by taking at least one of a sampling location, an area, a depth and a sample number into consideration in a case of vertically collected samples.

The sampling interval is determined by taking a compression rate of each sample according to the depth into consideration in the case of the vertically collected samples.

The method further includes the steps of making a contour map based on the statistical analysis result for the total concentration of the trace elements in horizontally collected samples; and confirming uniformity of the concentration of each trace element by using the contour map.

The method further includes the step of confirming uniformity of horizontally collected samples through a $\chi^2$ test, wherein $\chi^2$ test=$\Sigma\{(O-E)^2/E\}$, O is an observation value (analysis value) and E is an expectation value (average value).

The method further includes the step of confirming a variance of horizontally collected samples by using a box plot.

The horizontal sampling interval is regularly set within 30 m, the vertical sampling interval is set to at least 2 m, the sample number of vertically collected samples is at least 4, and an area for vertically collecting the samples is at least 500 $m^2$.

The method can be performed with respect to the samples collected in a single mine.

Advantages and/or characteristics of the present invention, and methods to accomplish them will be apparently comprehended by those skilled in the art when making reference to embodiments in the following description and accompanying drawings. However, the present invention is not limited to the following disclosed embodiments, but will be realized as various modifications. The present embodiments are provided to make the disclosure of the present invention perfect and to make those skilled in the art perfectly comprehend the scope of the present invention. The present invention is defined only within the scope of claims. Hereinafter, the same reference numerals will be assigned to the same elements throughout the whole specification.

As described above, according to one embodiment of the present invention, the number of samples to be collected can be determined and the representativeness of the collected sample can be verified when the sample is collected vertically and horizontally in the contaminated soil.

According to one embodiment of the present invention, the sampling method can be standardized by collecting samples at regular intervals according to the horizontal level (stratum) and the depth thereof from tailings of a single mine and performing the statistical analysis with respect to the concentration of the trace elements in the tailings to determine the horizontal/vertical sampling interval and the number of the samples standing for the tailings.

DETAILED DESCRIPTION OF THE INVENTION

Hereinafter, exemplary embodiments of the present invention will be described in detail with reference to accompanying drawings.

Figure 1:
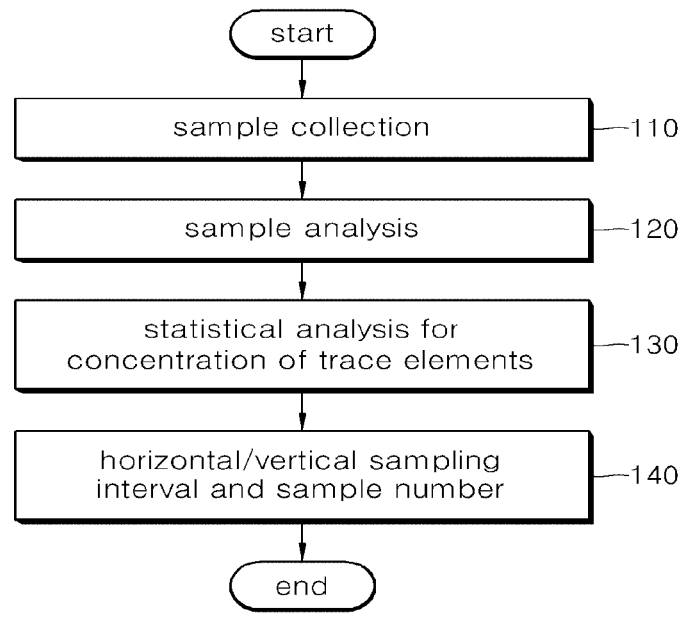
FIG. 1 is a flowchart for explaining a method for verifying representativeness of a sample collected in a contaminated soil according to one embodiment of the present invention.

FIG. 1 is a flowchart for explaining a method for verifying representativeness of a sample collected in a contaminated soil according to one embodiment of the present invention.

Referring to FIG. 1, the samples are horizontally and vertically collected from the soil on the basis of the stratum in a predetermined sampling interval in step 110.

In order to horizontally collect the samples, the sampling interval is regularly set, and the sampling interval in the horizontal direction is gradually increased.

In addition, in order to vertically collect the samples, the sampling interval is regularly set, and the sampling interval in the vertical direction is gradually increased.

In step 120, the collected samples are analyzed according to the sampling interval to measure the total concentration of the trace elements. The total concentration of the trace elements can be measured through the pretreatment using aqua regia and the chemical analysis using ICP-AES (inductively coupled plasma-atomic emission spectroscopy).

Then, in step 130, the statistics analysis is performed with respect to the total concentration of the trace elements. In order to perform the statistics analysis for the total concentration of the trace elements, the samples are sub-divided and it is compared whether the average concentration of the trace elements in each sub-group is identical to the average concentration of the trace elements in the total samples.

The sub-group may include samples selected by taking the sampling interval into consideration when the samples are horizontally collected. In addition, the sub-group may include samples selected by taking at least one of the sampling location, the sampling area, the sampling depth and the sample number when the samples are vertically collected.

Then, in step 140, the vertical and horizontal sampling interval and the sample number are determined based on the result of the statistics analysis. In the case of the samples, which are vertically collected, the sampling interval may be determined by taking the compression rate of each sample according to the depth into consideration.

According to one embodiment of the present invention, the horizontal sampling interval may be regularly determined within 30 m, and the vertical sampling interval may be at least 2 m. In addition, the sample number collected in the vertical direction is at least four and the vertical sampling area is at least 500 m$^2$.

1. Standardization of a Method for Collecting Samples from Tailings.

1-1 Introduction

More than thousand abandoned metal mines are distributed in Korea and many tailings are left in the abandoned metal mines. Thus, acid drainage and dissolved metals are discharged to the ambient environment from the tailings, causing serious damage to the ecosystem and the health of people around the mine. Therefore, it is necessary to determine the priority to rapidly and efficiently perform the contamination evaluation for the tailings existing in the abandoned metal mines.

In order to evaluate the contamination probability of the tailings, it is important to collect samples having representativeness from the tailings leaving in the abandoned metal mine. That is, the reasonable and systematic standardization for the sampling method and sample number must be set according to the characteristics (type of mineral deposits, kind of minerals, parent rock, etc.) of the tailings.

Most abandoned metal mines in Korea are distributed in the mountain regions having the difficulty of access, so the investigation, collection and transportation of the samples are very difficult. For this reason, it takes much time to collect the samples from the tailings leaving in the abandoned metal mines. In addition, information exerting influence upon contamination, such as information about the concentration of heavy metal standing for the tailings, can be obtained if the number of samples collected from the tailings is increased. However, if the analysis is performed with respect to the excessive amount of samples, much time and high cost may be resulted. Thus, in order to economically and rapidly evaluate the samples collected from the abandoned metal mines, the scientific and efficient sampling method standing for the tailing heap must be established.

According to the present invention, in order to establish the standardization of the sampling method, the samples are regularly collected according to the horizontal level (stratum) and the depth thereof from the tailings stacked in a large-size tailing heap of a Samgwang mine located at chungyang-gun, Chungcheongnam-do, and the statistical analysis is performed with respect to the trace elements in the tailings to determine the horizontal/vertical sampling interval and the number of the samples standing for the tailings.

1-2 Summary of Research Region

The Samgwang mine is located at sindae-ri, ungok-myun, chungyang-gun, Chungcheongnam-do. The Samgwang mine is one of the largest metal mines in Korea and had mined Au and Ag under the rule of Japanese imperialism and then abandoned in 2001. About 11 million tons of tailings and several thousand tons of mine wastes are heaped in the Samgwang mine, so contamination is propagated downstream of the Samgwang mine along the water system. In particular, the tailings and most of the soil around the Samgwang mine represent high As concentration. According to the previous research (ministry of environment, 2005), As concentration in the soil around the tailing heap was 15 to 25 times greater than the reference level, Pb concentration was two times greater than the reference level, and Cd concentration exceeded the reference level. In the case of paddy and dry fields in the vicinity of the tailing heap, the concentration exceeded the reference level by 20 times or more. The main reason of high concentration of AS in the Samgwang mine was the tailings. Since the tailings have been propagated to the ambient regions, the countermeasure for the tailings must be established through the precise investigation.

As to conditions for selecting the target mine to establish the standardization of the sampling method for the tailings, the tailing heap must have a large size to statistically treat the collected samples, and the trace elements must be contained in the tailings with high concentration. According to the report, the Samgwang mine has not yet been recovered, and has the large-size tailing heap with high concentration of As. Thus, the Samgwang mine is suitable for the present research and selected as the target mine.

1-3 Sampling and Statistic Measurement

The purpose of the standardization of the sampling method is to systematically and efficiently collect the samples having the representativeness of the tailings and to establish the sampling method applicable for all abandoned metal mines. To this end, the minimum number of samples having the representativeness is collected. That is, the minimum number of samples representing the characteristics of the tailings is collected to save the time and cost required for sampling work, and to reduce the cost for chemical analysis, thereby determining the priority for rapidly and accurately evaluating, recovering and treating the tailing heap.

(A) HORIZONTAL SAMPLING AND STATISTICAL CLASSIFICATION

Total 180 tailing samples (40M (meters)×95M (meters)) were collected at the sampling interval of 5M (meters) in the lattice pattern (5M (meters)×5M (meters)) from the tailing heap of the Samgwang mine. The sampling area was 3800 m$^2$ (see, table 1).

TABLE 1

Horizontal sampling location of tailings from Samgwang mine (total 180 samples)

| | | | | | | | | | | | | | | | | | | | |
|---|---|---|---|---|---|---|---|---|---|---|---|---|---|---|---|---|---|---|---|
| −1 | −1 | −1 | −1 | −1 | −1 | −1 | −1 | −1 | 0-1 | 1-1 | 2-1 | 3-1 | 4-1 | 5-1 | 6-1 | 7-1 | 8-1 | 9-1 | 0-1 |
| −2 | −2 | −2 | −2 | −2 | −2 | −2 | −2 | −2 | 0-2 | 1-2 | 2-2 | 3-2 | 4-2 | 5-2 | 6-2 | 7-2 | 8-2 | 9-2 | 0-2 |
| −3 | −3 | −3 | −3 | −3 | −3 | −3 | −3 | −3 | 0-3 | 1-3 | 2-3 | 3-3 | 4-3 | 5-3 | 6-3 | 7-3 | 8-3 | 9-3 | 0-3 |
| −4 | −4 | −4 | −4 | −4 | −4 | −4 | −4 | −4 | 0-4 | 1-4 | 2-4 | 3-4 | 4-4 | 5-4 | 6-4 | 7-4 | 8-4 | 9-4 | 0-4 |
| −5 | −5 | −5 | −5 | −5 | −5 | −5 | −5 | −5 | 0-5 | 1-5 | 2-5 | 3-5 | 4-5 | 5-5 | 6-5 | 7-5 | 8-5 | 9-5 | 0-5 |
| −6 | −6 | −6 | −6 | −6 | −6 | −6 | −6 | −6 | 0-6 | 1-6 | 2-6 | 3-6 | 4-6 | 5-6 | 6-6 | 7-6 | 8-6 | 9-6 | 0-6 |
| −7 | −7 | −7 | −7 | −7 | −7 | −7 | −7 | −7 | 0-7 | 1-7 | 2-7 | 3-7 | 4-7 | 5-7 | 6-7 | 7-7 | 8-7 | 9-7 | 0-7 |
| −8 | −8 | −8 | −8 | −8 | −8 | −8 | −8 | −8 | 0-8 | 1-8 | 2-8 | 3-8 | 4-8 | 5-8 | 6-8 | 7-8 | 8-8 | 9-8 | 0-8 |
| −9 | −9 | −9 | −9 | −9 | −9 | −9 | −9 | −9 | 0-9 | 1-9 | 2-9 | 3-9 | 4-9 | 5-9 | 6-9 | 7-9 | 8-9 | 9-9 | 0-9 |

The total concentration of the trace elements (As, Cd, Cu, Pb and Zn) in the tailing samples was analyzed and the standardization of the sampling method for the tailings having the representativeness was studied based on the total concentration through the statistical scheme. The total concentration was analyzed through the pretreatment using aqua regia and the chemical analysis using ICP-AES (inductively coupled plasma-atomic emission spectroscopy). Regarding the statistical scheme, the samples were sub-divided into sub-groups by arbitrarily setting the sampling interval and the average and variance of the total concentration of the trace elements in the samples of the sub-groups was compared with the average and variance of the total concentration of the tailings. In this research, the average concentration of the trace elements in the samples of each sampling interval was compared with the average concentration of the trace elements in all samples through the T-test.

In this research, the average concentration of the trace elements in the samples regularly collected at the interval of 5M (meters) was assumed as the concentration of the trace elements in the tailings. In addition, the average concentration of the trace elements in the samples regularly collected at the interval of 5M (meters) was compared with the average concentration and variance of the trace elements in the samples belonging to the sub-group, which was selected by gradually increasing the sampling interval in the unit of 5M (meters). In detail, on the assumption that the samples were collected at the interval of 10M (meters), 15M (meters), 20M (meters), 25M (meters), 30M (meters), 35M (meters) and 40M (meters), the samples belonging to each sub-group were classified and statistically measured to compare with all samples (that is, the tailings collected at the interval of 5M (meters)). As described above, 180 samples were collected from the tailing heap of the Samgwang mine, in which 50 samples were collected at the interval of 10M (meters), 21 samples were collected at the interval of 15M (meters), 15 samples were collected at the interval of 20M (meters), 12 samples were collected at the interval of 25M (meters), 8 samples were collected at the interval of 30M (meters), and 6 samples were collected at the interval of 35M (meters) and 40M (meters), respectively.

(B) VERTICAL SAMPLING AND STATISTICAL CLASSIFICATION

Figure 2:
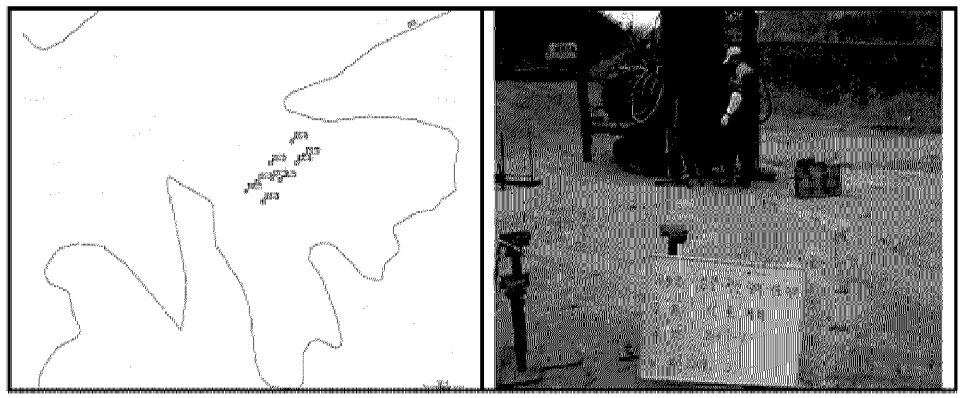
FIG. 2 is a view showing sampling locations according to depths and a working field.
Figure 3:
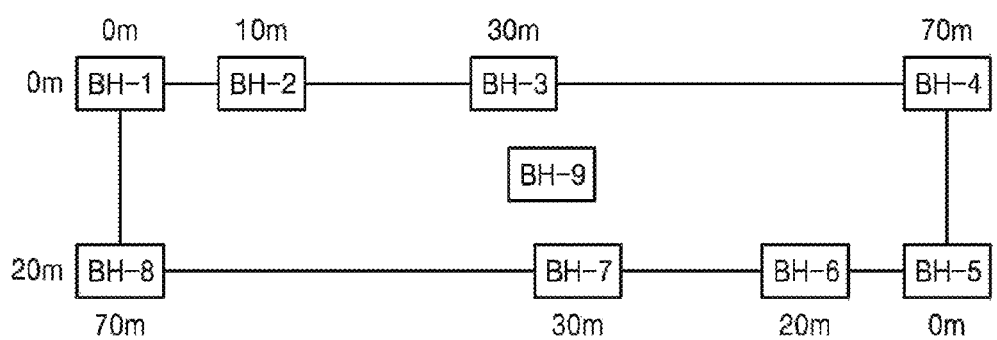
FIG. 3 is a view showing a detailed position of a coring sample.

The tailings were collected from the tailing heap of the Samgwang mine in the vertical direction in order to find the variation of the components of the trace elements in the vertical direction. The coring samples of the Samgwang mine were collected from 9 points. The coring samples were collected to the extent of the depth of 5M (meters), and the coring samples were separately sorted in each 1M (meters). The sampling location of the coring samples is shown in FIGS. 2 and 3. For reference, FIG. 2 is a view showing sampling locations according to depths and a working field, and FIG. 3 is a view showing a detailed position of the coring sample, in which the coring samples were collected while gradually widening the sampling interval in the unit of 10 m, 20 m and 40 m.

In order to find the vertical concentration of the trace elements in the tailings, each coring sample was analyzed per the depth of 50 cm. Thus, one coring sample represented 11 samples per the depth. Since nine coring samples were provided, 99 samples per the depth were provided.

Meanwhile, due to the pressure generated upon the coring, the length of coring samples is not uniform in each interval (1M (meters)). That is, the coring sample adjacent to the stratum was severely compressed, so that it had a short length and the coring sample collected from the deep depth had a length of about 1M (meters). Thus, the depth of the coring sample was determined proportionally to the length of each sample (interval 1M (meters)) by taking the compression rate into consideration.

For instance, if the actual length of the coring sample located from the stratum to the depth of 1M (meters) was 50 cm, the actual length of the core (5 cm) was assumed as 10 cm by taking the compression into consideration. Actually, an uppermost part (10 cm) and a middle part (10 cm) of the coring sample were used in each core interval (1M (meters)). In the case of the coring sample located in the depth of 4M (meters) to 5M (meters), a lowermost part (10 cm) of the coring sample was additionally analyzed. Thus, as described above, total 11 samples were analyzed per each coring sample according to the depth.

In order to establish the method for collecting the coring samples standing for the tailings, that is, in order to find the number of the coring samples having the representativeness, the number of the coring samples was variously classified and the average concentration and variance of the trace elements in the coring samples were compared with the average concentration and variance of the trace elements in the total samples (9 coring samples). The coring samples are sub-divided into sub-groups as shown in table 2 by taking the sampling locations into consideration.

TABLE 2 classification of sub-groups according to number of coring samples

| Sub-group | Sample number | Numbering |
|---|---|---|
| 1 | 5 | BH-1, 4, 5, 8 and 9 |
| 2 | 4 | BH-1, 4, 5 and 8 |
| 3 | 3 | BH-1, 5 and 9 |
| 4 | 3 | BH-4, 8 and 9 |
| 5 | 2 | BH-1 and 5 |
| 6 | 2 | BH-4 and 8 |
| 7 | 1 | BH-1 |
| 8 | 1 | BH-4 |
| 9 | 1 | BH-5 |
| 10 | 1 | BH-8 |
| 11 | 1 | BH-9 |

In order to establish the sampling method according to the depth, 9 coring samples per the depth of 0.5M (meters) were compared with total coring samples. That is, total 9 sub-groups were classified by increasing the depth in the unit of 0.5M (meters) from the stratum, and the average concentration and variance of the trace elements in the sub-groups were compared with the average concentration and variance of the trace elements in the total coring samples (depth 5M (meters) from the stratum). For instance, the first sub-group corresponded to the coring samples located from the stratum to the depth of 0.5M (meters), the second sub-group corresponded to the coring samples located from the stratum to the depth of 1M (meters), and the ninth sub-group corresponded to the coring samples located from the stratum to the depth of 4.5M (meters), so that total 9 sub-groups were classified.

In addition, in order to find the variation of the average concentration per the area, 11 sub-groups were classified according to the area as shown in table 3. In detail, the sub-groups having areas different from each other were classified by variously combining the sampling locations of the coring samples and the average concentration and variance of the trace elements in the coring samples were compared with the average concentration and variance of the trace elements in the total coring samples. For instance, the first sub-group had an area obtained by connecting BH-1, BH-2 and BH-8 shown in FIG. 3.

The difference between the average concentration of the trace elements in the sub-groups and the average concentration of the trace elements in the total coring samples according to the depth, the number and the area was found by using the T-test.

TABLE 3 classification of sub-groups according to area

| Sub-group | Sample number | area ($m^2$) | Numbering |
|---|---|---|---|
| 1 | 3 | 100 | BH-1, 2 and 8 |
| 2 | 3 | 300 | BH-1, 3 and 8 |
| 3 | 3 | 400 | BH-2, 3, 6 and 7 |
| 4 | 4 | 500 | BH-1, 2, 7 and 8 |
| 5 | 4 | 700 | BH-1, 4 and 8 |
| 6 | 4 | 700 | BH-1, 2, 6 and 8 |
| 7 | 4 | 700 | BH-1, 3, 7 and 8 |
| 8 | 4 | 700 | BH-1, 2, 5 and 8 |
| 9 | 4 | 900 | BH-1, 3, 6 and 8 |

TABLE 3-continued classification of sub-groups according to area

| Sub-group | Sample number | area (m²) | Numbering |
|---|---|---|---|
| 10 | 4 | 1,000 | BH-1, 3, 5 and 8 |
| 11 | 4 | 1,400 | BH-1, 4, 5 and 8 |

1-4 Result (A) Horizontal Contour Map of Tailings

Figure 4:
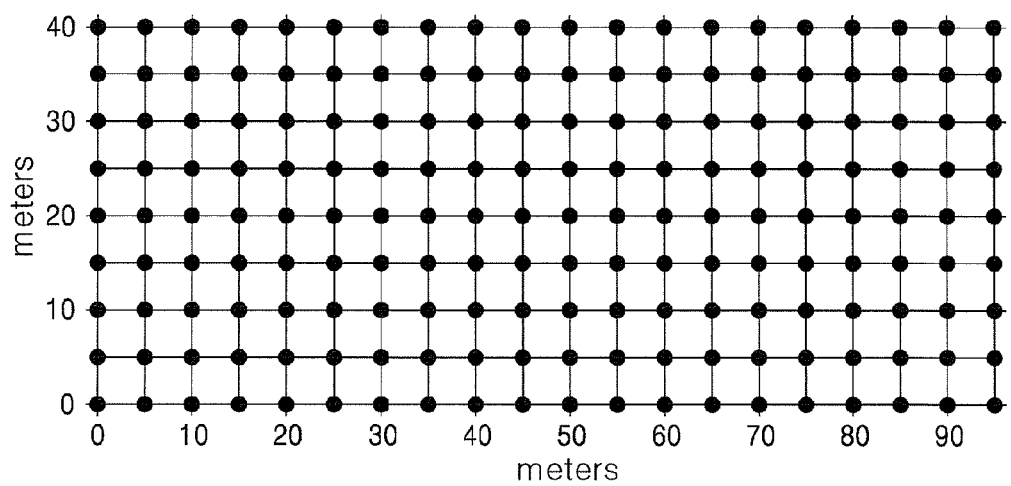
FIG. 4 is a view showing sampling locations for illustrating a contour map.

This research was performed to find the uniformity by using the contour map of the horizontal samples obtained from the Samgwang mine. To this end, As, Cd, Cu, Pb and Zn contained in the 180 samples collected at the interval of 5M (meters)×5M (meters) were analyzed and the contour map thereof was prepared by utilizing 'SURFER Program'. The contour map was obtained by utilizing the Kriging method and the sampling locations were shown in FIG. 4. For reference, FIG. 4 is a view showing the sampling locations for illustrating the contour map.

(1) As

Figure 5:
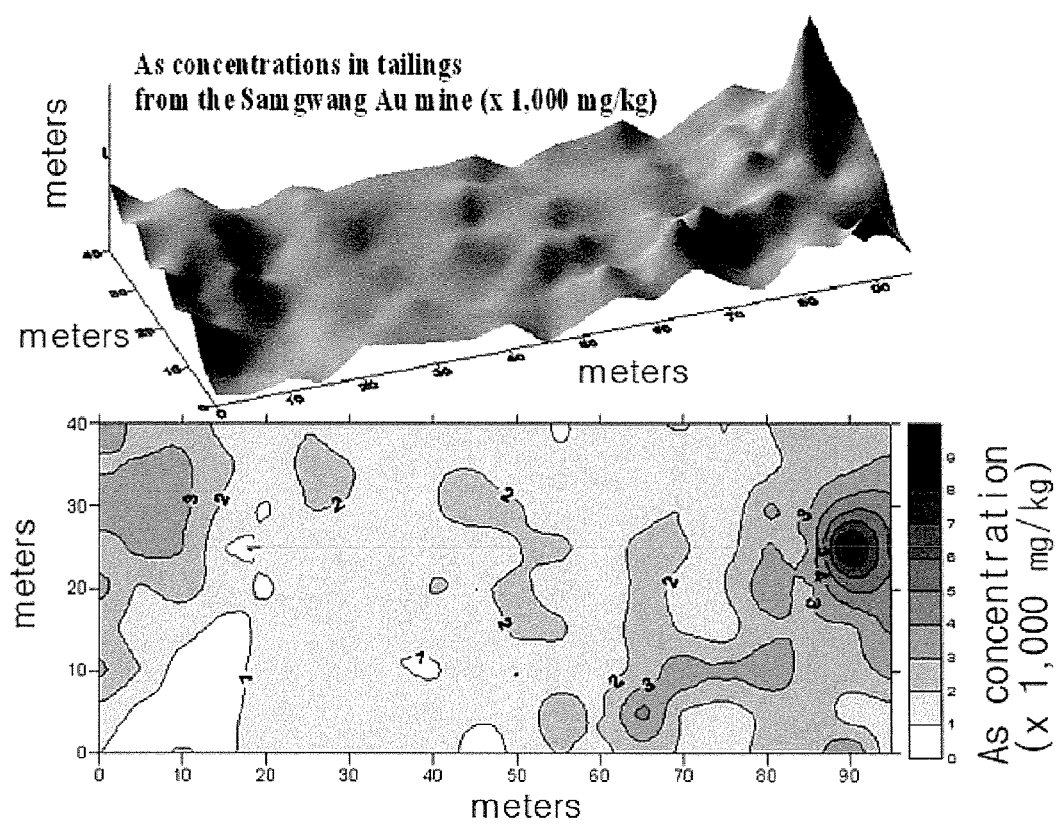
FIG. 5 is a view showing a contour map to illustrate As concentrations in tailings from the Samgwang mine.

FIG. 5 is a view showing the contour map to illustrate As concentrations in tailings from the Samgwang mine. As shown in FIG. 5, the As concentration was represented as 1000 to 2000 mg/kg in most regions. However, As having higher concentration was detected at the center of an end of a right side, representing the difference in uniformity. Nevertheless, except for this region, the As concentration is uniform in most regions.

(2) Cd

Figure 6:
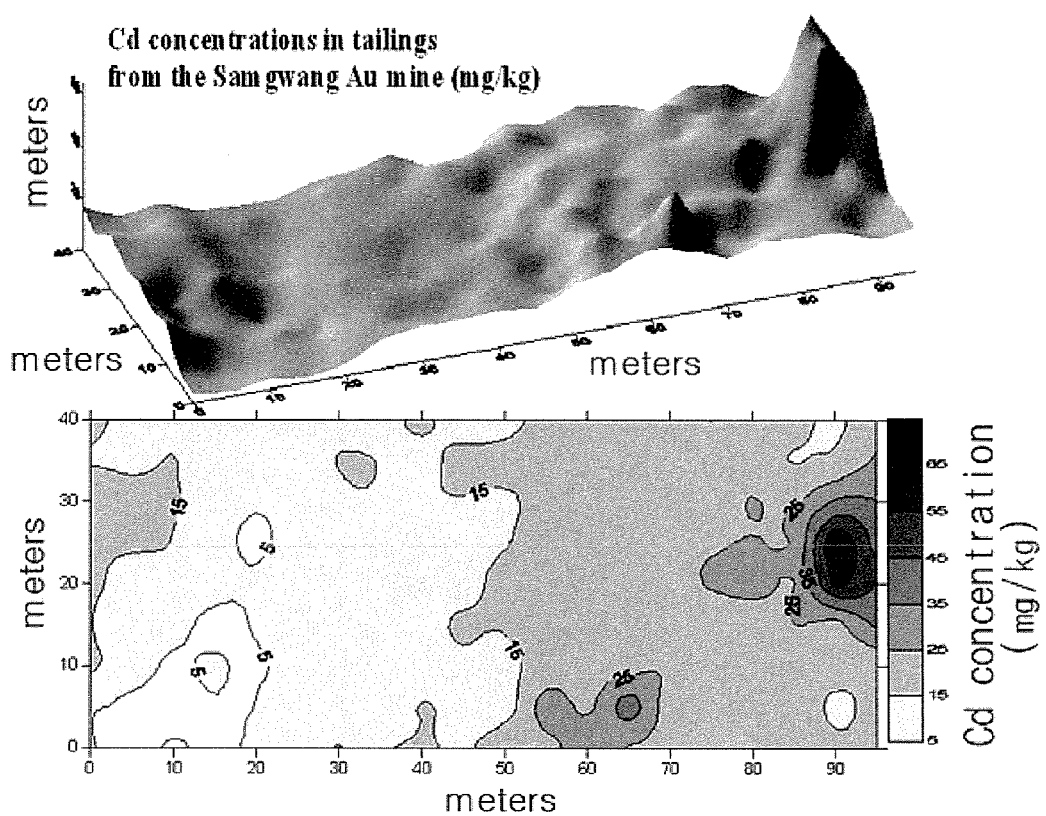
FIG. 6 is a view showing a contour map to illustrate Cd concentrations in tailings from the Samgwang mine.

FIG. 6 is a view showing the contour map to illustrate Cd concentrations in tailings from the Samgwang mine. As shown in FIG. 6, the Cd concentration was represented as 1.0 to 2.0 mg/kg in most regions. However, Cd having higher concentration was detected at the center of an end of a right side similar to the contour map of As, representing the difference in uniformity. Nevertheless, except for this region, the Cd concentration is uniform in most regions.

(3) Cu

Figure 7:
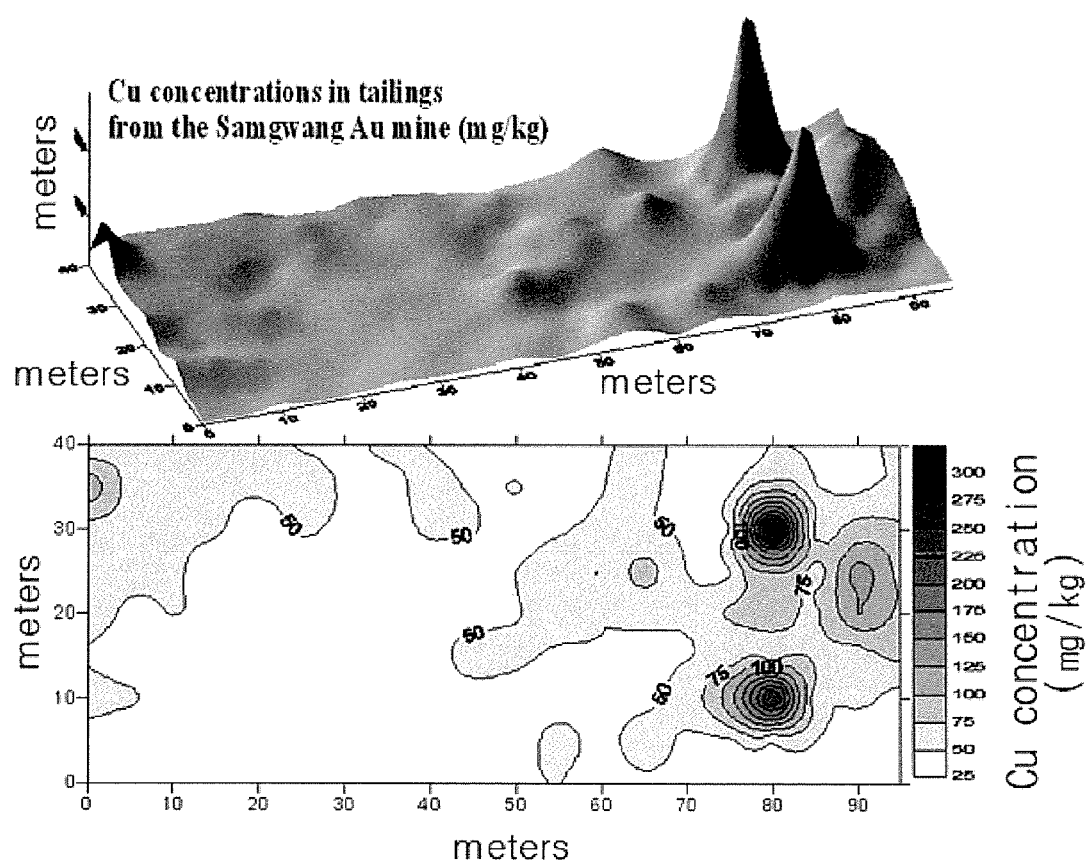
FIG. 7 is a view showing a contour map to illustrate Cu concentrations in tailings from the Samgwang mine.

FIG. 7 is a view showing the contour map to illustrate Cu concentrations in tailings from the Samgwang mine. As shown in FIG. 7, the Cu concentration was represented as about 50 mg/kg in most regions. However, Cu having higher concentration was detected at two points of an end of a right side, representing the difference in uniformity. Nevertheless, except for this region, the Cu concentration is uniform in most regions.

(4) Pb

Figure 8:
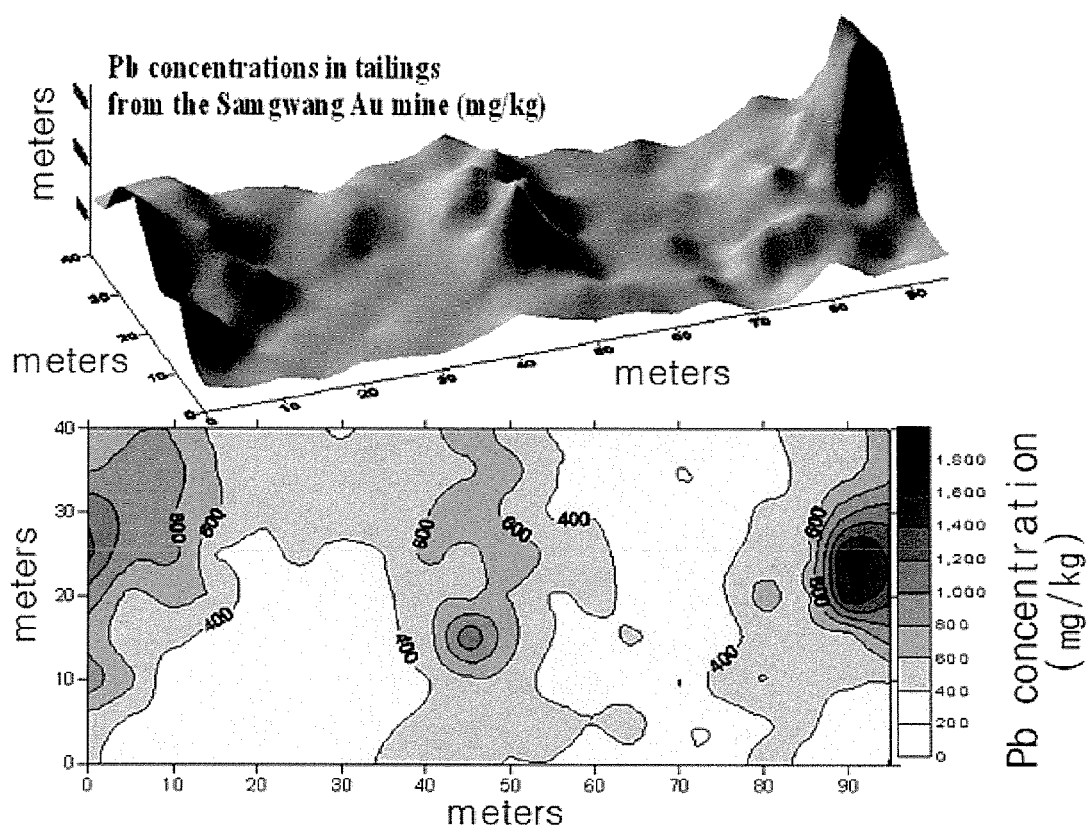
FIG. 8 is a view showing a contour map to illustrate Pb concentrations in tailings from the Samgwang mine.

FIG. 8 is a view showing the contour map to illustrate Pb concentrations in tailings from the Samgwang mine. As shown in FIG. 8, the Pb concentration was represented as about 500 mg/kg in most regions. However, Pb having higher concentration was detected at the center of an end of a right side similar to the contour maps of As and Cd, representing the difference in uniformity. Nevertheless, except for this region, the Pb concentration is uniform in most regions.

(5) Zn

Figure 9:
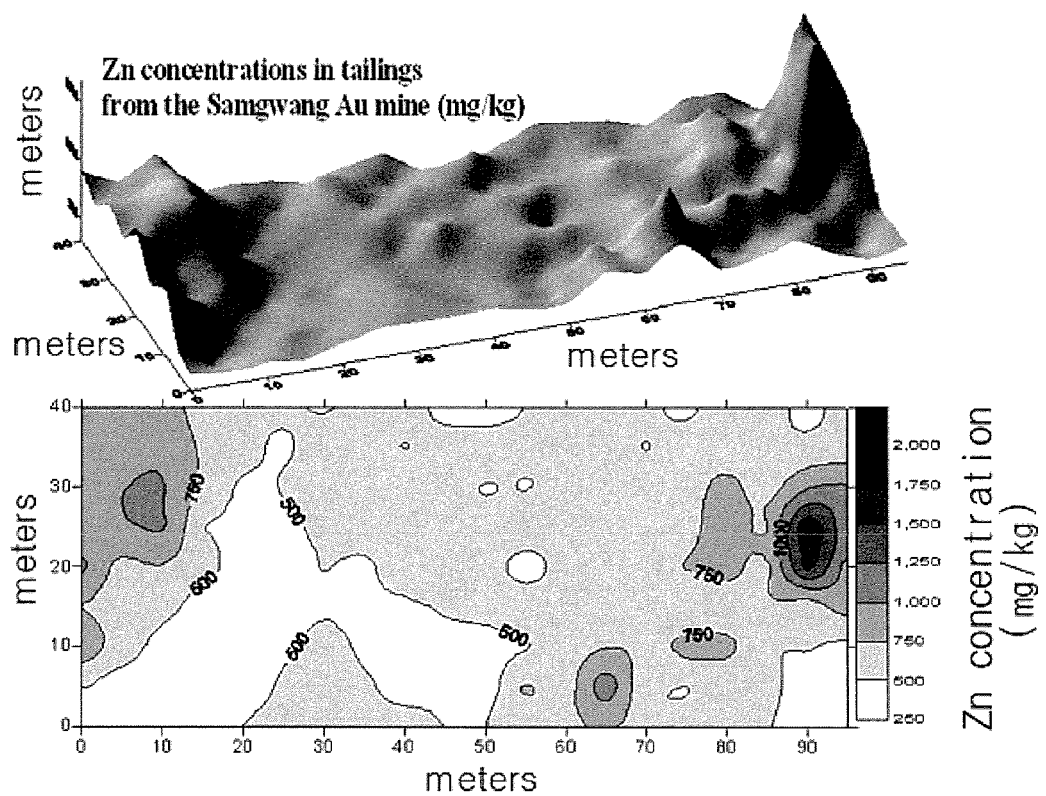
FIG. 9 is a view showing a contour map to illustrate Zn concentrations in tailings from the Samgwang mine.

FIG. 9 is a view showing the contour map to illustrate Zn concentrations in tailings from the Samgwang mine. As shown in FIG. 9, the Zn concentration was represented as about 500 mg/kg in most regions. However, Zn having higher concentration was detected at the center of an end of a right side similar to the contour maps of As Cd and Pb, representing the difference in uniformity. Nevertheless, except for this region, the Zn concentration is uniform in most regions.

(B) Uniformity Test Through $\chi^2$ Test

In order to check the uniformity of the horizontal sample, the $\chi^2$ test was utilized. In general, the $\chi^2$ test is the statistical scheme used for the uniformity test in a predetermined target region. The uniformity of the horizontal sample in each section was tested as follows.

$$\chi^2 \text{ test} = \Sigma\{(O-E)^2/E\}$$

In the above equation, O is an observation value (analysis value) and E is an expectation value (average value), and the $\chi^2$ test is defined as the sum of the values obtained by dividing the square value of (analysis value O-average value E) by the average value E.

In this research, 180 samples (20×9) were collected with the lattice interval of 5 m×5 m, and the concentration of As, Cd, Cu, Pb and Zn was measured. Among the measured values, the result of the $\chi^2$ test with respect to Cd and Zn is shown in table 4.

TABLE 4

$\chi^2$ test result

| element | Lattice interval | Lattice number(n) | $\chi^2$ value | $\chi^2$ test value (a = 0.05) | $\chi^2$ test value (a = 0.01) |
|---|---|---|---|---|---|
| Cd | 3 × 3 | 18 | 36.622 | 26.3 | 32.0 |
|  | 4 × 4 | 8 | 13.223 | 10.64 | 16.81 |
|  | 5 × 5 | 8 | 20.208 | 10.64 | 16.81 |
|  | 6 × 6 | 6 | 11.898 | 9.49 | 13.28 |
| Zn | 3 × 3 | 18 | 402.713 | 26.3 | 32.0 |
|  | 4 × 4 | 8 | 161.690 | 10.64 | 16.81 |
|  | 5 × 5 | 8 | 138.790 | 10.64 | 16.81 |
|  | 6 × 6 | 6 | 55.536 | 9.49 | 13.28 |

As shown in Table 4, the $\chi^2$ value in the significance level of 0.05 ($\alpha$=0.05) was higher than the text value, representing the difference of the uniformity. When the significance level was lowered to 0.01 in the lattice number of 3×3, the $\chi^2$ value was lower than the $\chi^2$ value in the lattice number of 4×4 and 6×6, representing the uniformity in a part of Cd.

However, in the case of Zn, the statistical similarity was not found in the uniformity test because the variance of the collected samples was excessively high. The above result was observed from most samples. That is, as a result of the analysis for the 180 samples, it was difficult to ensure the uniformity due to the concentration variation caused by high concentration. In detail, since the statistical scheme was performed on the assumption that the concentration of elements contained in the tailings in was similar to each other in the sampling regions, the above result was sufficiently expected because the uniformity of the samples may not be obtained in reality. In order to check whether the data have great variance, the box plot was utilized.

(2) Confirmation of Variance of Samples Through Box Plot

Figure 10:
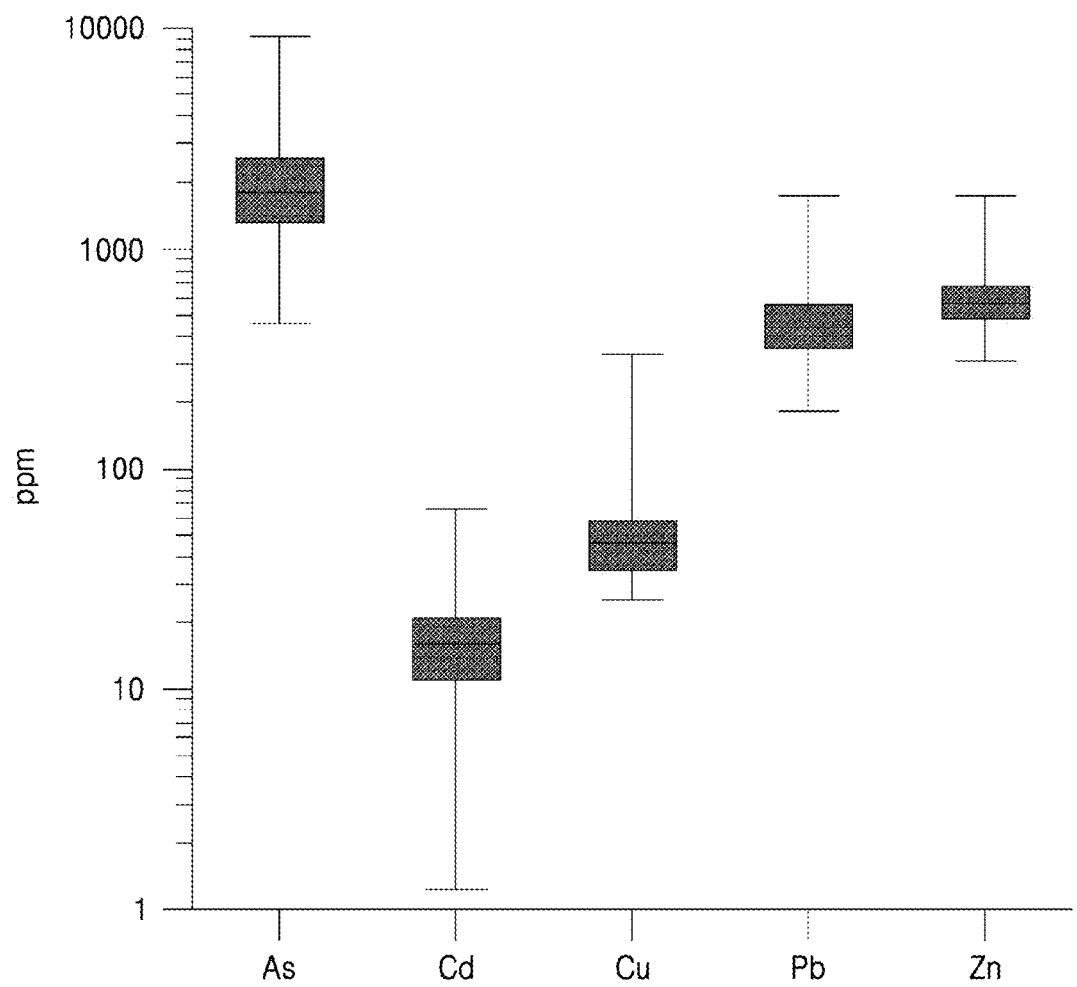
FIG. 10 is a graph showing a box plot to check variance of samples.

FIG. 10 is a graph showing the box plot to check the variance of samples. As shown in FIG. 10, when comparing with the box representing the central value and the range of 25% and 75% of the 180 samples, the value corresponding to the range of upper 25% and lower 25% is excessively high. Under the above circumstance, it is difficult to test the uniformity having the statistic significance. However, the $\chi^2$ test result represents that Cd has a relatively high uniformity in the samples having the interval of 20 m×20 m and 25 m×25 m.

(C) OPTIMUM HORIZONTAL SAMPLING METHOD

Figure 11:
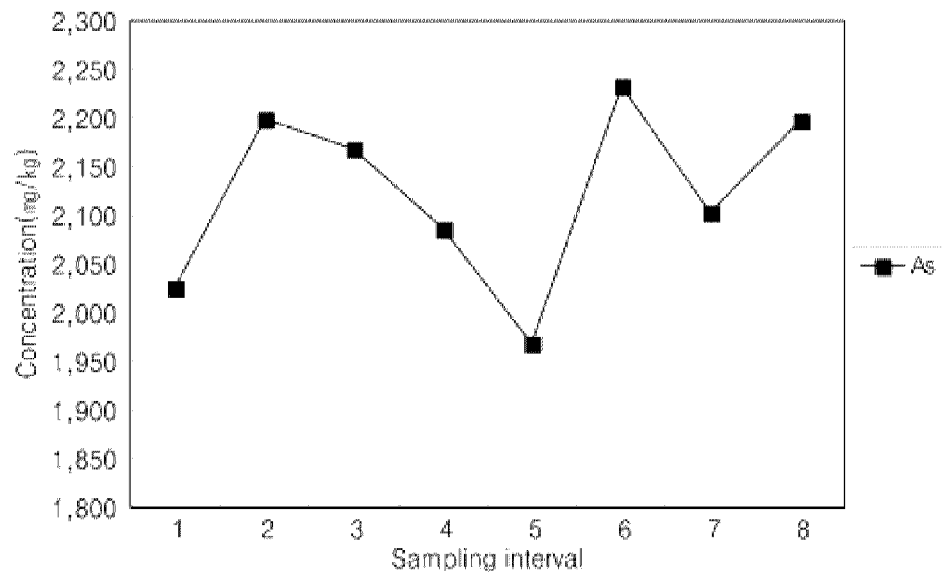
FIGS. 11 to 13 are graphs showing statistics values of trace elements in a sample horizontally collected from a tailing.
Figure 12:
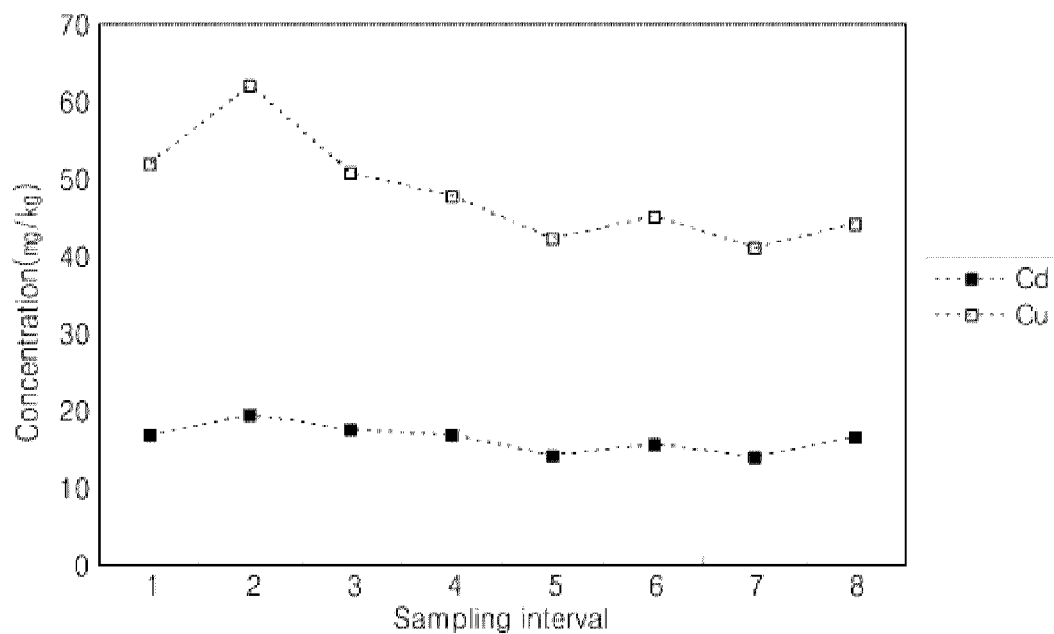
Figure 13:
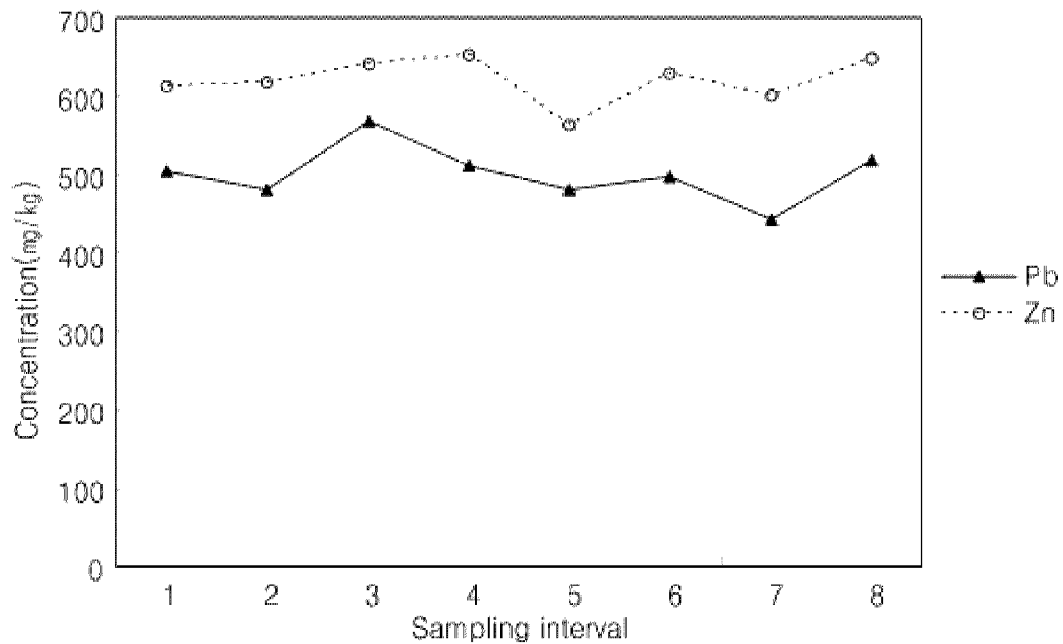

The statistic values for the concentration of the trace elements in the samples horizontally collected from the tailings are shown in Table 5 and FIGS. 11 to 13.

TABLE 5

Statistic values for concentration (ppm) of trace elements
according to horizontal (stratum) sampling interval

| Sampling Interval (M) | Statistics | As | Cd | Cu | Pb | Zn |
|---|---|---|---|---|---|---|
| 5 | AVG | 2,026 | 17 | 52 | 504 | 613 |
|   | STD | 1,081 | 9 | 33 | 251 | 203 |
|   | CV | 0.53 | 0.54 | 0.64 | 0.50 | 0.33 |
|   | MAX | 9,167 | 66 | 330 | 1,756 | 1,734 |
|   | MIN | 459 | 1 | 25 | 184 | 310 |
| 10 | AVG | 2,199 | 19 | 62 | 480 | 617 |
|   | STD | 1,088 | 9 | 54 | 263 | 234 |
|   | CV | 0.495 | 0.48 | 0.88 | 0.55 | 0.38 |
|   | MAX | 5,125 | 58.4 | 329.8 | 1,610.7 | 1,601.7 |
|   | MIN | 592 | 2 | 26 | 184 | 326 |
|   | T statistic | 0.996 | 0.099 | 0.708 | 0.320 | 0.687 |
|   | p-value | 0.322 | 0.921 | 0.481 | 0.750 | 0.494 |
| 15 | AVG | 2,168 | 17 | 51 | 567 | 642 |
|   | STD | 1,814 | 12 | 28 | 364 | 299 |
|   | CV | 0.84 | 0.70 | 0.56 | 0.64 | 0.47 |
|   | MAX | 9,167 | 66 | 142 | 1,756 | 1,734 |
|   | MIN | 592 | 7 | 28 | 213 | 411 |
|   | T statistic | 0.351 | 0.236 | −0.182 | 0.768 | 0.432 |
|   | p-value | 0.729 | 0.816 | 0.857 | 0.451 | 0.670 |
| 20 | AVG | 2,087 | 17 | 48 | 512 | 653 |
|   | STD | 966 | 8 | 18 | 173 | 174 |
|   | CV | 0.46 | 0.49 | 0.38 | 0.34 | 0.27 |
|   | MAX | 3,883 | 31 | 98 | 943 | 1,072 |
|   | MIN | 907 | 5 | 30 | 306 | 417 |
|   | T statistic | 0.232 | −0.002 | −0.800 | 0.165 | 0.851 |
|   | p-value | 0.819 | 0.998 | 0.432 | 0.871 | 0.407 |
| 25 | AVG | 1,968 | 14 | 42 | 481 | 564 |
|   | STD | 927 | 5 | 12 | 200 | 196 |
|   | CV | 0.47 | 0.33 | 0.28 | 0.42 | 0.35 |
|   | MAX | 3,883 | 21 | 60 | 717 | 932 |
|   | MIN | 883 | 7 | 28 | 213 | 326 |
|   | T statistic | −0.171 | −1.502 | −1.989 | −0.314 | −0.688 |
|   | p-value | 0.869 | 0.164 | 0.068 | 0.761 | 0.511 |
| 30 | AVG | 2,233 | 16 | 45 | 498 | 630 |
|   | STD | 958 | 3 | 11 | 217 | 204 |
|   | CV | 0.43 | 0.19 | 0.23 | 0.43 | 0.32 |
|   | MAX | 3,883 | 19 | 62 | 959 | 949 |
|   | MIN | 1,300 | 11 | 34 | 329 | 412 |
|   | T statistic | 0.594 | −0.917 | −1.528 | −0.080 | 0.233 |
|   | p-value | 0.569 | 0.375 | 0.149 | 0.938 | 0.822 |
| 35 | AVG | 2,103 | 14 | 41 | 443 | 602 |
|   | STD | 914 | 6 | 10 | 169 | 163 |
|   | CV | 0.43 | 0.40 | 0.23 | 0.38 | 0.27 |
|   | MAX | 3,883 | 20 | 56 | 686 | 932 |
|   | MIN | 1,368 | 6 | 30 | 206 | 510 |
|   | T statistic | 0.201 | −1.168 | −2.379 | −0.855 | −0.169 |
|   | p-value | 0.849 | 0.287 | 0.039 | 0.425 | 0.871 |
| 40 | AVG | 2,197 | 17 | 44 | 519 | 649 |
|   | STD | 1,009 | 6 | 7 | 121 | 156 |
|   | CV | 0.46 | 0.37 | 0.16 | 0.23 | 0.24 |
|   | MAX | 3,883 | 22 | 51 | 686 | 932 |
|   | MIN | 1,001 | 5 | 31 | 336 | 467 |
|   | T statistic | 0.406 | −0.088 | −2.021 | 0.272 | 0.550 |
|   | p-value | 0.701 | 0.933 | 0.063 | 0.794 | 0.602 |

The average concentration of As according to the horizontal sampling interval was higher than the average concentration of As in the total tailings and the tendency was irregular (See, FIG. 13). This is caused by non-uniform distribution of As in the tailings.

In the case of Cu, the average concentration of Cu according to the sampling interval was lower than the average concentration of Cu in the total tailing. Although the concentration of Cu had the lower value of 52 mg/kg, there was relatively high difference in the average concentration of Cu according to the sampling interval, so it was determined that the concentration of Cu is not uniform in the tailings. In the case of Cd, there was little difference in the average concentration of Cd according to the sampling interval, so it was determined that the concentration of Cd is uniform in the tailings. Meanwhile, in the case of Pb and Zn, the difference in the average concentration of Pb and Zn according to the sampling interval was relatively high, but it was more uniform than that of As.

According to the above result, the variation in concentration of the trace elements in the tailings had no specific tendency, but various tendencies were represented from the trace elements. Thus, it may be difficult to determine the sampling method standing for the tailings by using the variation of the average concentration of the trace elements.

Figure 14:
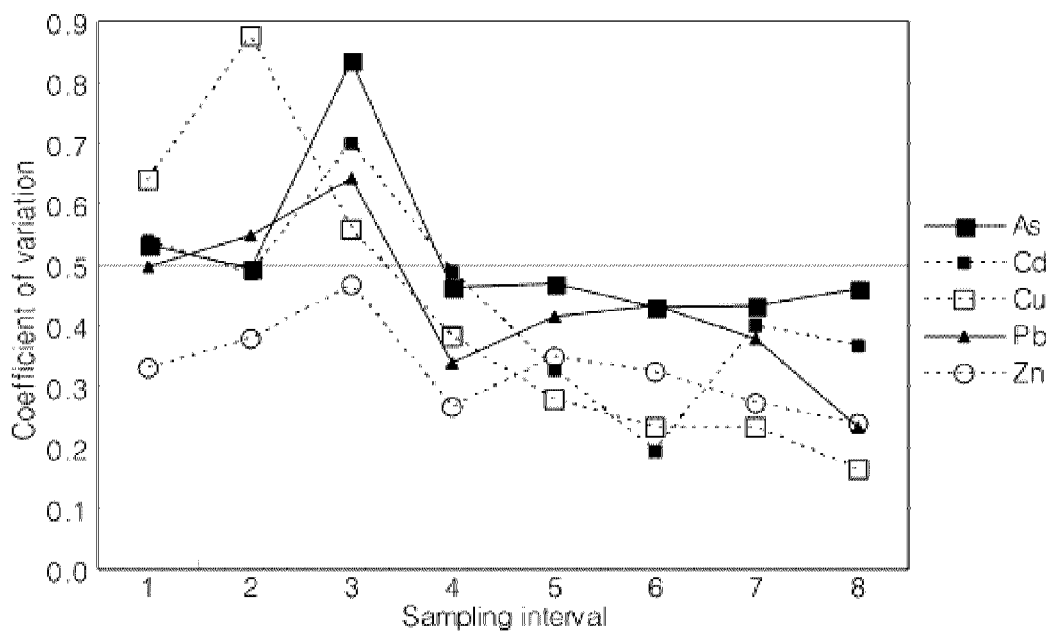
FIG. 14 is a graph showing the coefficient of variation as a function of the horizontal sampling interval.

FIG. 14 is a graph showing the coefficient of variation (C.V.) as a function of the horizontal sampling interval.

As shown in FIG. 14, the coefficient of variation of all trace elements, as a whole, was reduced as the sampling interval was increased (that is, as the sample number was reduced). However, the coefficient of variation was increased in the sampling intervals of 10M (meters) and 15M (meters). In the case of Cd, the coefficient of variation was increased in the sampling interval of 35M (meters) (number 7 in the x-axis). This reflects that the concentration of the trace elements in the tailings was non-uniform.

Meanwhile, as represented the higher variation of coefficient as compared with other trace elements in each sampling interval and Cu also represented the higher variation of coefficient in the sampling interval of 10M (meters). Among the trace elements, Cu represented the highest variation of coefficient according to the sample interval and remaining trace elements represented similar variation of coefficient. The above result indicates that the concentration of Cu and As was more irregular than the concentration of other trace elements, so it is necessary to pay attention to Cu and As when determining the sampling method having the representativeness.

Figure 15:
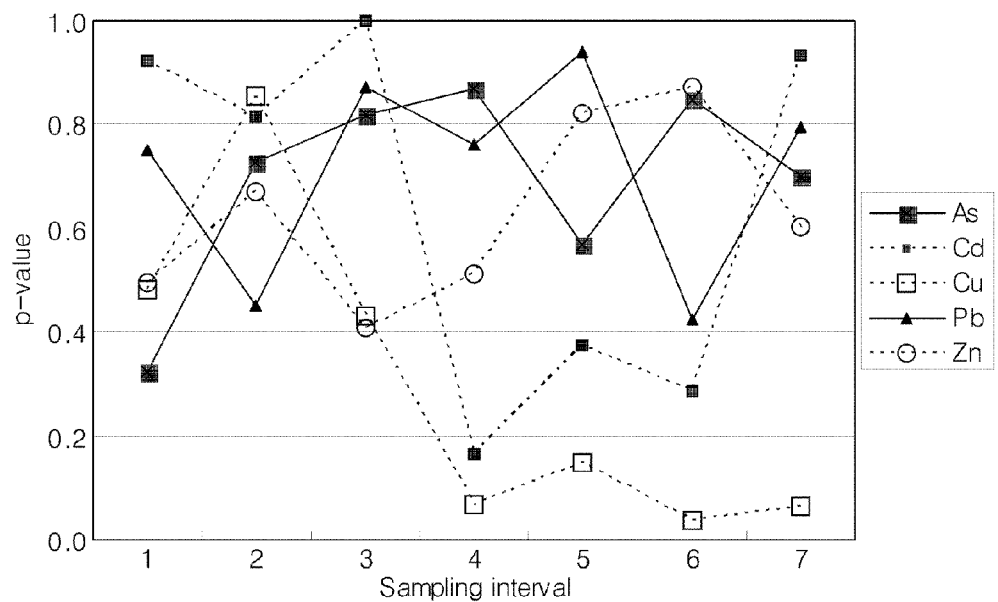
FIG. 15 is a graph showing the p-value as a function of the horizontal sampling interval.

FIG. 15 is a graph showing the p-value as a function of the horizontal sampling interval.

As shown in FIG. 15, in most cases, the p-value (significance probability) according to the horizontal sampling interval was higher than 0.05. However, when the sample was collected at the interval of 35M (meters) (that is, number 6 in x-axis), the p-value of Cu was 0.039, which is lower than 0.05. This result indicates that the concentration of Cu was significantly different from the average concentration in the samples when the sample was collected at the interval of 35M (meters). Thus, the samples standing for the tailings can be obtained only when the samples are collected at the interval of 30M (meters) or less.

However, since the average concentration of As in the tailings had a higher value of 2000 mg/kg or above and concentration of As and Cu was relatively irregular, the method for collecting the samples from the tailings must be carefully determined.

In other words, even if the samples are collected at the regular interval, the result may vary depending on sampling parts of the tailing heap. Thus, the investigation must be performed several times while varying the sampling interval in various manners to confirm whether the same result can be obtained. In addition, when the samples are collected in the outdoor field, the selection of the sampling locations based on the grain size of the tailings and mineral identification is very important. That is, the samples must be collected from the location where many sulfide minerals exist.

(D) OPTIMUM VERTICAL SAMPLING METHOD (CORE SAMPLE)

Figure 16:
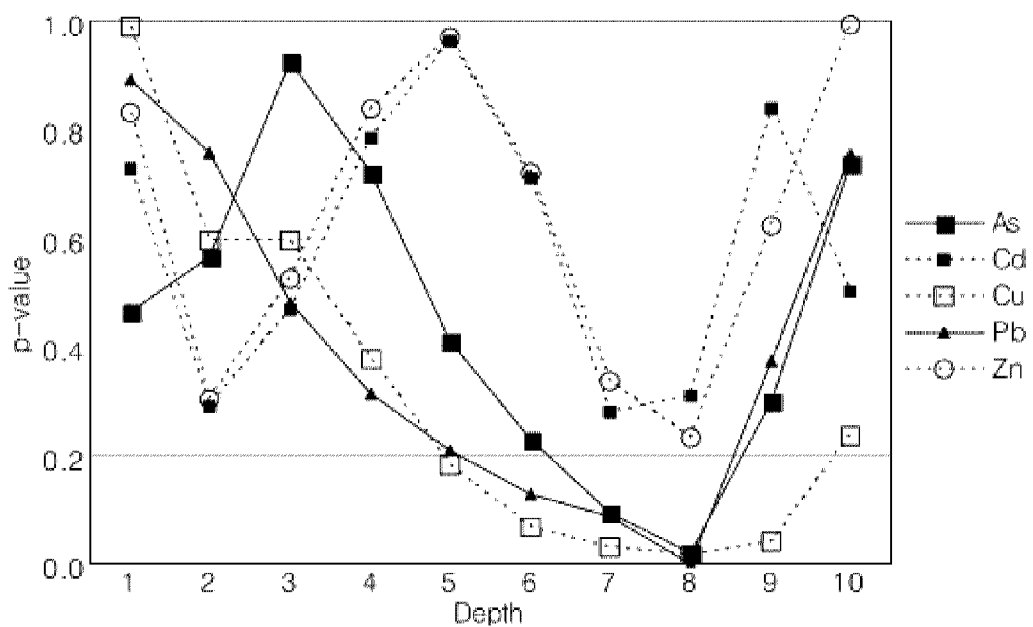
FIGS. 16 to 18 are graphs showing statistics values of trace elements in a sample vertically collected from a tailing.
Figure 17:
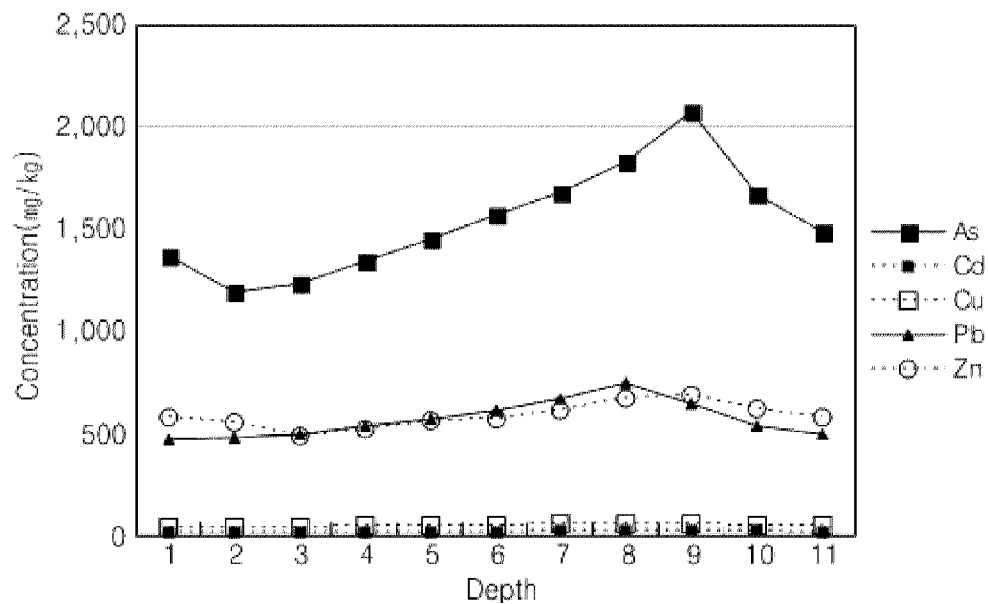
Figure 18:
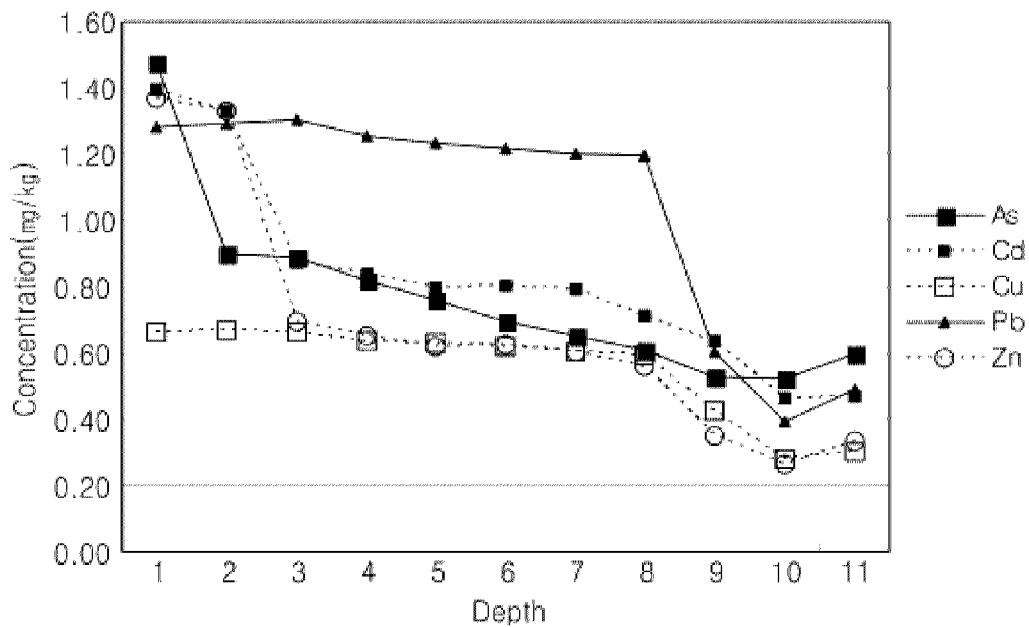

The statistic values for the concentration of the trace elements in the samples vertically collected from the tailings are shown in Table 6 and FIGS. 16 to 18.

TABLE 6

Statistic value for variation of average concentration of trace elements according to depth of core samples

| Depth | | As | Cd | Cu | Pb | Zn |
|---|---|---|---|---|---|---|
| 5M | Avg | 1,370 | 21 | 44 | 467 | 578 |
| | Std | 2,025 | 29 | 29 | 598 | 791 |
| | Cv | 1.48 | 1.40 | 0.66 | 1.28 | 1.37 |
| | Max | 18,104 | 213 | 205 | 5,495 | 6,656 |
| | Min | 13 | 0 | 8 | 75 | 51 |
| | median | 901 | 14 | 38 | 368 | 425 |
| 4.5M | Avg | 1,198 | 19 | 44 | 479 | 555 |
| | Std | 1,079 | 26 | 29 | 621 | 739 |
| | Cv | 0.90 | 1.33 | 0.67 | 1.30 | 1.33 |
| | Max | 4,696 | 213 | 205 | 5,495 | 6,656 |
| | Min | 13 | 0 | 12 | 82 | 51 |
| | Median | 899 | 14 | 38 | 381 | 423 |
| | T statistic | −0.732 | −0.351 | 0.011 | 0.135 | −0.213 |
| | p-value | 0.466 | 0.726 | 0.991 | 0.893 | 0.831 |
| 4.0M | Avg | 1,233 | 17 | 44 | 496 | 488 |
| | Std | 1,096 | 15 | 29 | 647 | 338 |
| | Cv | 0.89 | 0.87 | 0.66 | 1.30 | 0.69 |
| | Max | 4,696 | 86 | 205 | 5,495 | 2,324 |
| | Min | 13 | 0 | 12 | 82 | 51 |
| | Median | 924 | 14 | 38 | 388 | 420 |
| | T statistic | 0.573 | 1.060 | −0.533 | −0.310 | 1.032 |
| | p-value | 0.567 | 0.291 | 0.595 | 0.757 | 0.304 |
| 3.5M | Avg | 1,347 | 18 | 47 | 538 | 522 |
| | Std | 1,103 | 15 | 30 | 674 | 341 |
| | Cv | 0.82 | 0.84 | 0.64 | 1.25 | 0.65 |
| | Max | 4,696 | 86 | 205 | 5,495 | 2,324 |
| | Min | 26 | 1 | 12 | 82 | 86 |
| | Median | 1,081 | 15 | 41 | 418 | 483 |
| | T statistic | −0.095 | −0.728 | 0.533 | 0.708 | −0.636 |
| | p-value | 0.925 | 0.467 | 0.595 | 0.480 | 0.526 |
| 3.0M | Avg | 1,458 | 20 | 49 | 576 | 560 |
| | Std | 1,109 | 16 | 31 | 711 | 347 |
| | Cv | 0.76 | 0.79 | 0.63 | 1.23 | 0.62 |
| | Max | 4,696 | 86 | 205 | 5,495 | 2,324 |
| | Min | 26 | 1 | 15 | 84 | 86 |
| | Median | 1,202 | 17 | 44 | 434 | 506 |
| | T statistic | 0.358 | −0.274 | 0.885 | 1.010 | −0.203 |
| | p-value | 0.721 | 0.785 | 0.378 | 0.315 | 0.840 |

TABLE 6-continued

Statistic value for variation of average concentration
of trace elements according to depth of core samples

| Depth | | As | Cd | Cu | Pb | Zn |
|---|---|---|---|---|---|---|
| 2.5M | Avg | 1,578 | 21 | 51 | 618 | 575 |
| | Std | 1,096 | 17 | 32 | 754 | 359 |
| | Cv | 0.69 | 0.80 | 0.62 | 1.22 | 0.62 |
| | Max | 4,696 | 86 | 205 | 5,495 | 2,324 |
| | Min | 28 | 1 | 15 | 84 | 86 |
| | Median | 1,385 | 17 | 45 | 473 | 508 |
| | T statistic | 0.823 | −0.045 | 1.347 | 1.269 | −0.039 |
| | p-value | 0.412 | 0.964 | 0.181 | 0.208 | 0.969 |
| 2.0M | Avg | 1,687 | 22 | 55 | 676 | 613 |
| | Std | 1,099 | 18 | 33 | 813 | 369 |
| | Cv | 0.65 | 0.79 | 0.60 | 1.20 | 0.60 |
| | Max | 4,696 | 86 | 205 | 5,495 | 2,324 |
| | Min | 93 | 1 | 16 | 84 | 86 |
| | Median | 1,469 | 19 | 49 | 526 | 576 |
| | T statistic | 1.212 | 0.373 | 1.848 | 1.544 | 0.360 |
| | p-value | 0.227 | 0.710 | 0.068 | 0.127 | 0.719 |
| 1.5M | Avg | 1,835 | 25 | 59 | 747 | 676 |
| | Std | 1,117 | 18 | 35 | 893 | 377 |
| | Cv | 0.61 | 0.71 | 0.59 | 1.20 | 0.56 |
| | Max | 4,696 | 86 | 205 | 5,495 | 2,324 |
| | Min | 197 | 4 | 16 | 84 | 94 |
| | Median | 1,921 | 22 | 50 | 534 | 646 |
| | T statistic | 1.683 | 1.086 | 2.239 | 1.740 | 0.966 |
| | p-value | 0.095 | 0.280 | 0.029 | 0.088 | 0.336 |
| 1.0M | Avg | 2,076 | 25 | 58 | 649 | 689 |
| | Std | 1,098 | 16 | 25 | 393 | 241 |
| | Cv | 0.53 | 0.64 | 0.43 | 0.61 | 0.35 |
| | Max | 4,696 | 77 | 154 | 2,052 | 1,308 |
| | Min | 197 | 4 | 31 | 191 | 263 |
| | Median | 2,127 | 22 | 54 | 559 | 662 |
| | T statistic | 2.354 | 1.022 | 2.477 | 4.260 | 1.197 |
| | p-value | 0.021 | 0.310 | 0.017 | 0.000 | 0.234 |
| 0.5M | Avg | 1674 | 22 | 54 | 537 | 622 |
| | Std | 873 | 10 | 15 | 211 | 163 |
| | Cv | 0.52 | 0.46 | 0.28 | 0.39 | 0.26 |
| | Max | 2,939 | 44 | 83 | 1,009 | 850 |
| | Min | 197 | 6 | 33 | 191 | 263 |
| | Median | 1,729 | 21 | 51 | 521 | 655 |
| | T statistic | 1.049 | 0.205 | 2.096 | 0.897 | 0.493 |
| | p-value | 0.299 | 0.838 | 0.042 | 0.373 | 0.623 |
| 0.0M | Avg | 1492 | 18 | 52 | 500 | 579 |
| | Std | 894 | 8 | 16 | 246 | 194 |
| | Cv | 0.60 | 0.47 | 0.30 | 0.49 | 0.33 |
| | Max | 2,939 | 32 | 83 | 1,009 | 850 |
| | Min | 284 | 6 | 36 | 191 | 263 |
| | Median | 1422 | 16 | 46 | 526 | 560 |
| | T statistic | 0.339 | −0.681 | 1.235 | 0.318 | 0.009 |
| | p-value | 0.738 | 0.501 | 0.237 | 0.754 | 0.993 |

As shown in FIG. 16, the p-value of As, Cu and Pb was lower than 0.05 at the depth of 1.0M (number 8 in x-axis), representing that the concentration of As, Cu and Pb was different from the average concentration in the samples. In particular, the p-value of Cu was lower than 0.05 at the depth in the range of 0.5M to 1.5M. Thus, when taking the uniformity of all trace elements into consideration, the samples must be collected at the depth of at least 2.0M or above.

As shown in FIG. 16, the p-value of As, Cu and Pb was lower than 0.05 at the depth of 1.0M (meters) (number 8 in x-axis), representing that the concentration of As, Cu and Pb was different from the average concentration in the samples. In particular, the p-value of Cu was lower than 0.05 at the depth in the range of 0.5M (meters) to 1.5M (meters). Thus, when taking the uniformity of all trace elements into consideration, the samples must be collected at the depth of at least 2.0M (meters) or above.

Referring to FIG. 17, as the depth had become shallow, that is, as the depth had become reduced to the level of about 1.5M (meters), the concentration of the trace elements was increased. In particular, the concentration of As was significantly increased as the depth had become reduced to the level of 1.0M (meters). Meanwhile, the concentration of the trace elements was decreased as the depth is reduced below 1.0M (meters). In the cases of Pb and Zn, the average concentration according to the depth was similar to that of As. In contrast, the average concentration of Cd and Cu according to the depth was not significantly changed.

FIG. 18 is a view showing the variation of concentration of the trace elements as a function of the depth (increased by 50 cm from the right to the left in the x-axis). Referring to FIG. 18, the concentration was significantly increased at the depth of 1.5M (meters). In particular, Pb represented a higher value above 1.0.

Meanwhile, the concentration of other trace elements was increased until the depth reached 2.0M (meters). In addition, the concentration of other trace elements was constant as the depth was increased more than 2.0M (meters).

TABLE 7

Statistic value for variation of average concentration of trace elements according to number of core samples

| Sample | Statistic | As | Cd | Cu | Pb | Zn |
|---|---|---|---|---|---|---|
| 9 | Avg | 1,370 | 21 | 44 | 467 | 578 |
|  | Std | 2,025 | 29 | 29 | 598 | 791 |
|  | Cv | 1.48 | 1.40 | 0.66 | 1.28 | 1.37 |
|  | Max | 18,104 | 213 | 205 | 5,495 | 6,656 |
|  | Min | 13 | 0 | 8 | 75 | 51 |
|  | Median | 901 | 14 | 38 | 368 | 425 |
| 5 | Avg | 1,417 | 28 | 54 | 577 | 707 |
|  | Std | 2,577 | 37 | 34 | 765 | 1,023 |
|  | Cv | 1.82 | 1.35 | 0.63 | 1.33 | 1.45 |
|  | Max | 18,104 | 213 | 205 | 5,495 | 6,656 |
|  | Min | 26 | 1 | 15 | 84 | 51 |
|  | Median | 637 | 16 | 51 | 442 | 442 |
|  | T statistic | 0.117 | 1.144 | 1.812 | 0.917 | 0.809 |
|  | p-value | 0.907 | 0.256 | 0.073 | 0.362 | 0.421 |
| 4 | Avg | 1,583 | 29 | 53 | 567 | 762 |
|  | Std | 2,847 | 41 | 37 | 842 | 1,130 |
|  | Cv | 1.80 | 1.41 | 0.70 | 1.48 | 1.48 |
|  | Max | 18,104 | 213 | 205 | 5,495 | 6,656 |
|  | Min | 26 | 1 | 15 | 84 | 86 |
|  | Median | 712 | 16 | 45 | 418 | 437 |
|  | T statistic | 0.449 | 1.177 | 1.329 | 0.712 | 0.977 |
|  | p-value | 0.655 | 0.244 | 0.188 | 0.479 | 0.332 |
| 3 | Avg | 1,267 | 22 | 52 | 632 | 563 |
|  | Std | 1,206 | 18 | 34 | 930 | 458 |
|  | Cv | 0.95 | 0.85 | 0.66 | 1.47 | 0.81 |
|  | Max | 4,696 | 86 | 205 | 5,495 | 2,324 |
|  | Min | 26 | 1 | 15 | 107 | 51 |
|  | Median | 899 | 16 | 45 | 442 | 442 |
|  | T statistic | −0.351 | 0.155 | 1.121 | 0.955 | −0.141 |
|  | p-value | 0.726 | 0.877 | 0.268 | 0.345 | 0.888 |
| 3 | Avg | 1,345 | 32 | 59 | 534 | 779 |
|  | Std | 3,164 | 46 | 30 | 390 | 1,254 |
|  | Cv | 2.35 | 1.43 | 0.52 | 0.73 | 1.61 |
|  | Max | 18,104 | 213 | 154 | 2,052 | 6,656 |
|  | Min | 37 | 1 | 15 | 84 | 51 |
|  | Median | 383 | 19 | 60 | 447 | 480 |
|  | T statistic | −0.043 | 1.284 | 2.393 | 0.733 | 0.862 |
|  | p-value | 0.966 | 0.207 | 0.020 | 0.465 | 0.394 |
| 2 | Avg | 1,525 | 21 | 47 | 641 | 600 |
|  | Std | 1,345 | 20 | 39 | 1,125 | 522 |
|  | Cv | 0.88 | 0.92 | 0.83 | 1.75 | 0.87 |
|  | Max | 4,696 | 86 | 205 | 5,495 | 2,324 |
|  | Min | 26 | 3 | 15 | 107 | 88 |
|  | Median | 1,075 | 16 | 41 | 400 | 437 |
|  | T statistic | −0.311 | 0.101 | 0.350 | 0.703 | 0.158 |
|  | p-value | 0.760 | 0.920 | 0.729 | 0.489 | 0.875 |
| 2 | Avg | 1,642 | 37 | 58 | 494 | 924 |
|  | Std | 3,844 | 54 | 35 | 416 | 1,512 |
|  | Cv | 2.34 | 1.47 | 0.60 | 0.84 | 1.64 |
|  | Max | 18,104 | 213 | 154 | 2,052 | 6,656 |
|  | Min | 37 | 1 | 15 | 84 | 86 |
|  | Median | 332 | 19 | 59 | 436 | 445 |
|  | T statistic | 0.322 | 1.314 | 1.713 | 0.244 | 1.041 |
|  | p-value | 0.750 | 0.202 | 0.098 | 0.809 | 0.308 |
| 1 | Avg | 1,823 | 25 | 60 | 1,002 | 650 |
|  | Std | 1,318 | 24 | 51 | 1,526 | 612 |
|  | Cv | 0.72 | 0.97 | 0.86 | 1.52 | 0.94 |
|  | Max | 4,696 | 86 | 205 | 5,495 | 2,324 |
|  | Min | 235 | 8 | 22 | 177 | 202 |
|  | Median | 1,529 | 16 | 41 | 494 | 442 |
|  | T statistic | 1.013 | 0.487 | 0.999 | 1.153 | 0.356 |
|  | p-value | 0.326 | 0.634 | 0.339 | 0.276 | 0.727 |
| 1 | Avg | 2,549 | 49 | 48 | 320 | 1,389 |
|  | Std | 5,288 | 71 | 36 | 240 | 2,061 |
|  | Cv | 2.07 | 1.45 | 0.75 | 0.75 | 1.48 |
|  | Max | 18,104 | 213 | 114 | 730 | 6,656 |
|  | Min | 37 | 1 | 15 | 84 | 86 |
|  | Median | 430 | 16 | 26 | 325 | 560 |
|  | T statistic | 0.733 | 1.304 | 0.315 | −1.568 | 1.294 |
|  | p-value | 0.480 | 0.222 | 0.758 | 0.129 | 0.225 |
| 1 | Avg | 1,227 | 18 | 35 | 280 | 550 |
|  | Std | 1,366 | 15 | 15 | 208 | 440 |
|  | Cv | 1.11 | 0.83 | 0.43 | 0.74 | 0.80 |
|  | Max | 3,840 | 56 | 60 | 732 | 1,629 |
|  | Min | 26 | 3 | 15 | 107 | 88 |

TABLE 7-continued

Statistic value for variation of average concentration
of trace elements according to number of core samples

| Sample | Statistic | As | Cd | Cu | Pb | Zn |
|---|---|---|---|---|---|---|
| | Median | 427 | 16 | 30 | 191 | 420 |
| | T statistic | 0.733 | −0.511 | −1.785 | −2.152 | −0.183 |
| | p-value | 0.480 | 0.615 | 0.089 | 0.039 | 0.857 |
| 1 | Avg | 734 | 23 | 68 | 667 | 459 |
| | Std | 1,121 | 22 | 32 | 490 | 282 |
| | Cv | 1.53 | 0.95 | 0.47 | 0.73 | 0.61 |
| | Max | 3,919 | 77 | 154 | 2,052 | 1,116 |
| | Min | 93 | 1 | 31 | 246 | 94 |
| | Median | 284 | 19 | 65 | 506 | 411 |
| | T statistic | −0.993 | 0.333 | 2.361 | 0.116 | −1.024 |
| | p-value | 0.335 | 0.745 | 0.036 | 0.231 | 0.313 |
| 1 | Avg | 751 | 22 | 60 | 615 | 488 |
| | Std | 643 | 15 | 20 | 335 | 296 |
| | Cv | 0.86 | 0.71 | 0.34 | 0.54 | 0.61 |
| | Max | 2,313 | 44 | 91 | 1,060 | 962 |
| | Min | 171 | 1 | 27 | 108 | 51 |
| | Median | 499 | 21 | 60 | 609 | 509 |
| | T statistic | −2.195 | 0.180 | 2.370 | 1.253 | −0.761 |
| | p-value | 0.034 | 0.859 | 0.032 | 0.226 | 0.453 |

Figure 19:
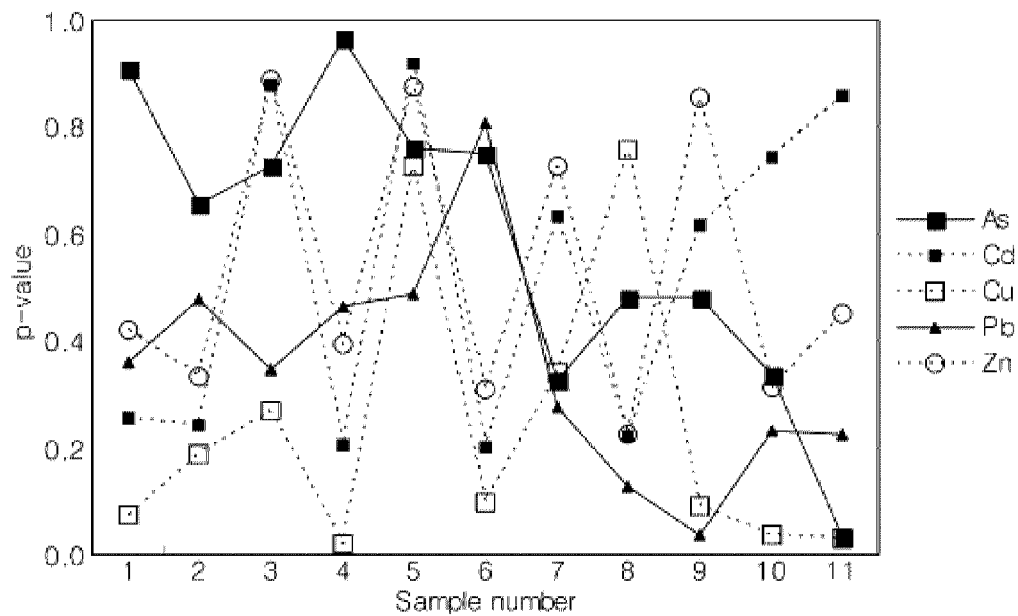
FIG. 19 is a graph showing the p-value as a function of the coring sample number.

FIG. 19 is a graph showing the p-value as a function of the coring sample number.

As shown in FIG. 19, when one coring sample was collected, the p-value of As, Cu and Pb was lower than 0.05. In the case of Cu, the p-value is 0.020 when three samples were collected, so the average concentration of Cu was different from the average concentration in all samples (nine samples). Thus, Cu may not stand for all samples. Therefore, at least four coring samples must be collected by taking the representativeness of all trace elements into consideration.

Figure 20:
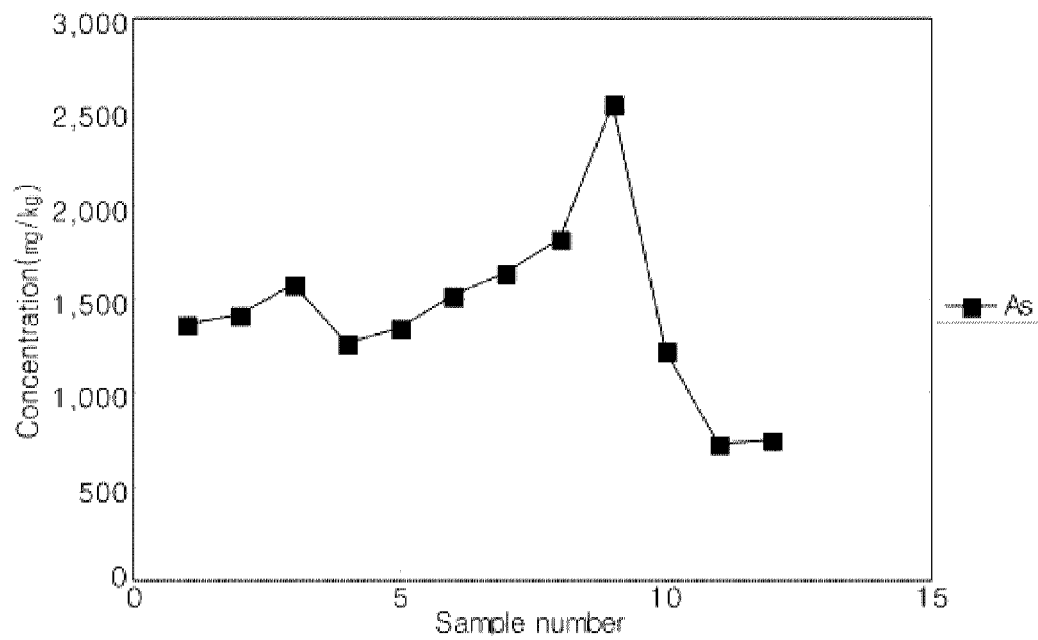
FIGS. 20 to 22 are graphs showing concentration of trace elements as a function of the coring sample number.
Figure 21:
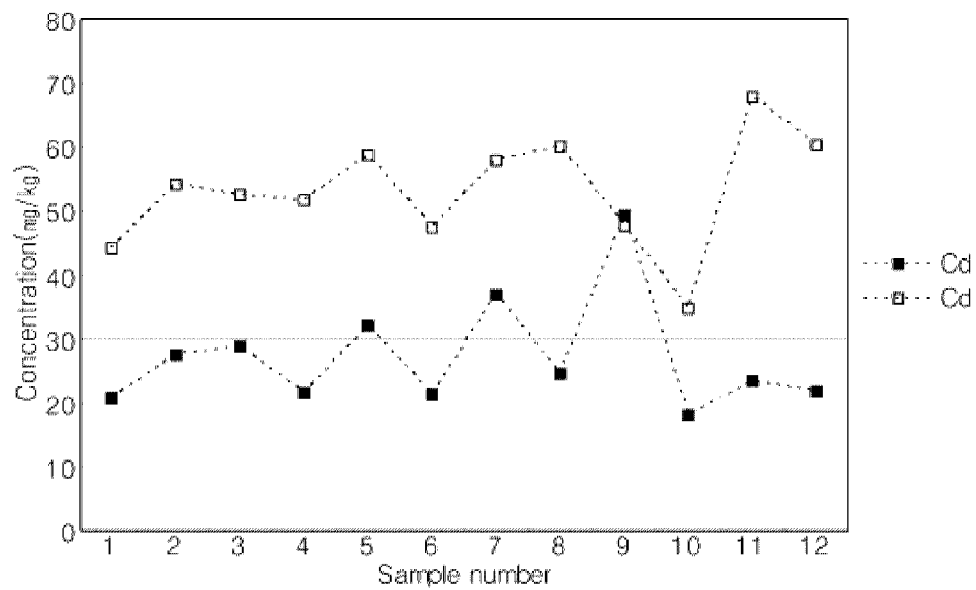
Figure 22:
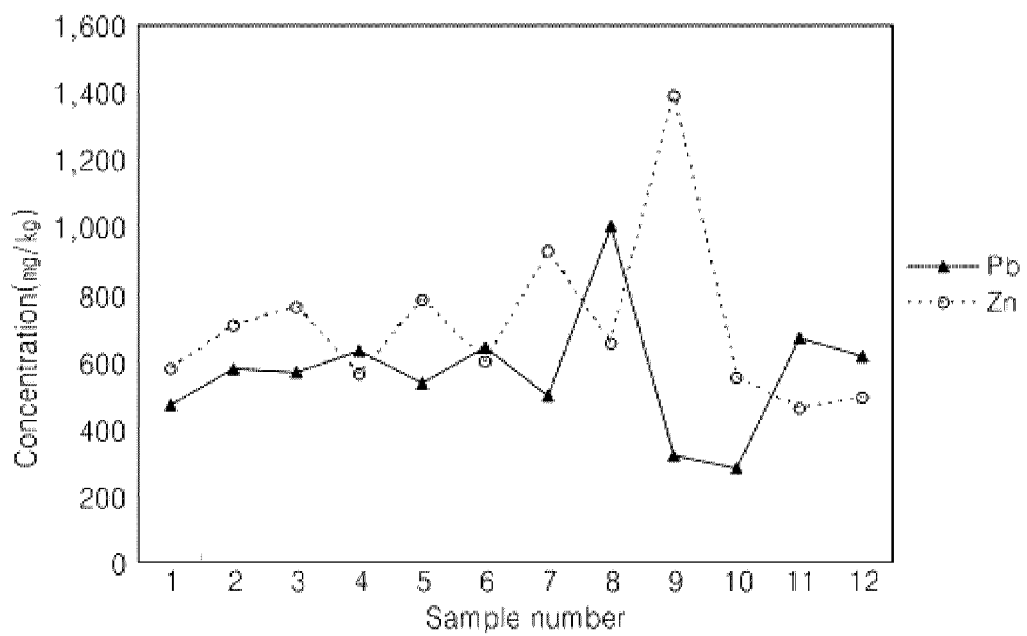

FIGS. 20 to 22 are graphs showing the concentration of the trace elements as a function of the coring sample number.

As shown in FIGS. 20 to 22, the average concentration of the trace elements in one coring sample was very irregular. However, the average concentration of the trace elements in two coring samples was substantially constant although there was slight variation.

In detail, the number of samples having the average concentration of the trace elements similar to the average concentration of the trace elements in all core samples (As: 1370, Cd: 21, Cu: 44, Pb: 467, and Zn: 578) was three (in case of As), two (in case of Cd), two (in case of Pb) and three (in case of Zn), which was similar to the value obtained from two to three samples through the statistic measurement. Thus, it is necessary to collect at least three coring samples, which is similar to the result of T-test representing the collection of at least four samples.

Figure 23:
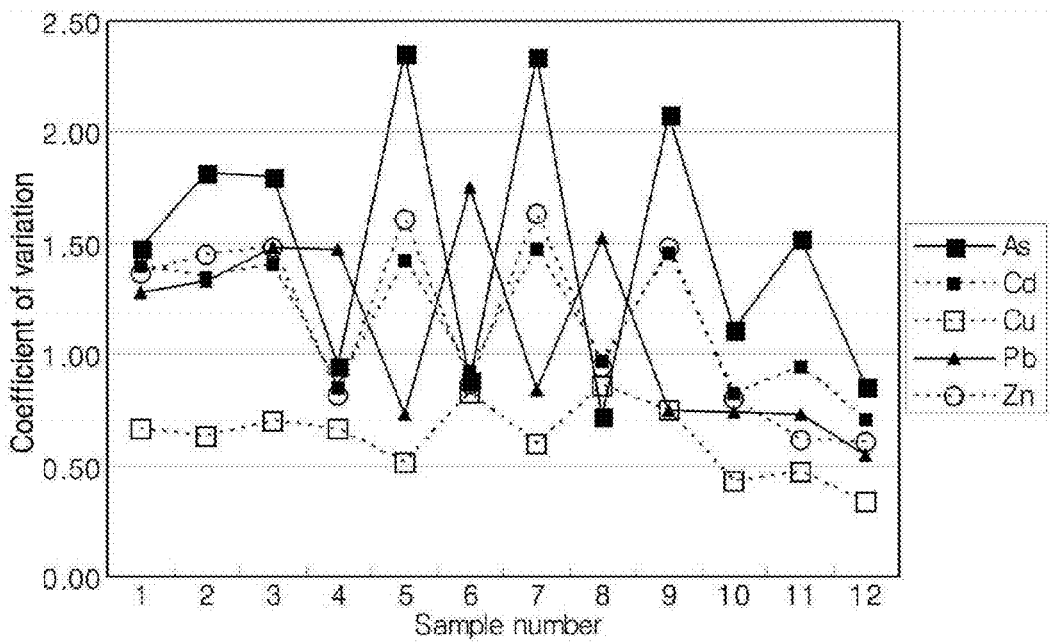
FIG. 23 is a graph showing the coefficient of variation as a function of the sample number.

FIG. 23 is a graph showing the coefficient of variation as a function of the sample number.

As shown in FIG. 23, the coefficient of variation was very irregular as a function of the sample number. In particular, the coefficient of variation of As was significant changed as a function of the sample number. Further, Pb and Zn also represent significant variation as a function of the sample number. The above result was derived from the non-uniformity of the tailings. In addition, since the total concentration of the trace elements was relatively high, the standard deviation was also high, so the significant variation was resulted.

TABLE 8

Statistic value for variation of average concentration
of trace elements according to area of core samples

| Area | Statistic | As | Cd | Cu | Pb | Zn |
|---|---|---|---|---|---|---|
| 1,400 | Avg | 1,370 | 21 | 44 | 467 | 578 |
| | Std | 2,025 | 29 | 29 | 598 | 791 |
| | Cv | 1.48 | 1.40 | 0.66 | 1.28 | 1.37 |
| | Max | 18,104 | 213 | 205 | 5,495 | 6,656 |
| | Min | 13 | 0 | 8 | 75 | 51 |
| | Median | 901 | 14 | 38 | 368 | 425 |
| 1,400 (11) | Avg | 1,583 | 29 | 53 | 567 | 762 |
| | Std | 2,847 | 41 | 37 | 842 | 1,130 |
| | Cv | 1.80 | 1.41 | 0.70 | 1.48 | 1.48 |
| | Max | 18,104 | 213 | 205 | 5,495 | 6,656 |
| | Min | 26 | 1 | 15 | 84 | 86 |
| | Median | 712 | 16 | 45 | 418 | 437 |
| | T statistic | −0.449 | −1.177 | −1.329 | −0.712 | −0.977 |
| | p-value | 0.655 | 0.244 | 0.188 | 0.479 | 0.332 |
| 1,000 (10) | Avg | 1,334 | 20 | 50 | 586 | 539 |
| | Std | 1,243 | 18 | 34 | 837 | 419 |
| | Cv | 0.93 | 0.89 | 0.69 | 1.43 | 0.78 |
| | Max | 4,696 | 86 | 205 | 5,495 | 2,324 |
| | Min | 26 | 1 | 13 | 79 | 83 |
| | median | 955 | 17 | 44 | 438 | 462 |

TABLE 8-continued

Statistic value for variation of average concentration of trace elements according to area of core samples

| Area | Statistic | As | Cd | Cu | Pb | Zn |
|---|---|---|---|---|---|---|
| | T statistic | 0.128 | 0.123 | −0.919 | −0.846 | 0.393 |
| | p-value | 0.898 | 0.903 | 0.361 | 0.401 | 0.695 |
| 900 (9) | Avg | 1,321 | 19 | 49 | 589 | 504 |
| | Std | 1,180 | 18 | 35 | 835 | 389 |
| | Cv | 0.89 | 0.93 | 0.72 | 1.42 | 0.77 |
| | Max | 4,696 | 86 | 205 | 5,495 | 2,324 |
| | Min | 13 | 1 | 8 | 75 | 83 |
| | Median | 955 | 16 | 42 | 438 | 443 |
| | T statistic | 0.180 | 0.123 | −0.768 | −0.875 | 0.756 |
| | p-value | 0.858 | 0.903 | 0.445 | 0.385 | 0.451 |
| 700 (8) | Avg | 1,279 | 20 | 49 | 578 | 510 |
| | Std | 1,219 | 18 | 34 | 839 | 411 |
| | Cv | 0.95 | 0.93 | 0.70 | 1.45 | 0.81 |
| | Max | 4,696 | 86 | 205 | 5,495 | 2,324 |
| | Min | 26 | 1 | 14 | 101 | 88 |
| | Median | 856 | 16 | 42 | 429 | 426 |
| | T statistic | 0.331 | 0.502 | −0.810 | −0.789 | 0.677 |
| | p-value | 0.741 | 0.616 | 0.420 | 0.433 | 0.499 |
| 700 (7) | Avg | 1,323 | 18 | 48 | 583 | 497 |
| | Std | 1,136 | 18 | 35 | 837 | 390 |
| | Cv | 0.86 | 0.98 | 0.74 | 1.43 | 0.78 |
| | Max | 4,696 | 86 | 205 | 5,495 | 2,324 |
| | Min | 16 | 0 | 12 | 79 | 58 |
| | Median | 1,156 | 14 | 40 | 427 | 437 |
| | T statistic | 0.176 | 0.270 | −0.553 | −0.831 | 0.826 |
| | p-value | 0.861 | 0.788 | 0.582 | 0.409 | 0.410 |
| 700 (6) | Avg | 1,266 | 18 | 48 | 582 | 475 |
| | Std | 1,156 | 18 | 35 | 837 | 379 |
| | Cv | 0.91 | 0.97 | 0.73 | 1.44 | 0.80 |
| | Max | 4,696 | 86 | 205 | 5,495 | 2,324 |
| | Min | 13 | 1 | 8 | 75 | 94 |
| | Median | 856 | 14 | 40 | 429 | 418 |
| | T statistic | 0.386 | 0.662 | −0.661 | −0.818 | 1.054 |
| | p-value | 0.700 | 0.509 | 0.511 | 0.416 | 0.294 |
| 700 (5) | Avg | 1,702 | 33 | 59 | 663 | 833 |
| | Std | 3,201 | 46 | 40 | 949 | 1,279 |
| | Cv | 1.88 | 1.41 | 0.69 | 1.43 | 1.54 |
| | Max | 18,104 | 213 | 205 | 5,495 | 6,656 |
| | Min | 37 | 1 | 15 | 84 | 86 |
| | Median | 788 | 17 | 55 | 457 | 442 |
| | T statistic | −0.560 | 0.651 | −1.889 | −1.113 | −1.076 |
| | p-value | 0.579 | 0.516 | 0.065 | 0.272 | 0.288 |
| 500 (4) | Avg | 1,268 | 18 | 47 | 576 | 468 |
| | Std | 1,113 | 18 | 35 | 838 | 378 |
| | Cv | 0.88 | 1.02 | 0.74 | 1.46 | 0.81 |
| | Max | 4695.65 | 85.79 | 204.63 | 5494.64 | 2323.91 |
| | Min | 16 | 0 | 12 | 82 | 58 |
| | Median | 1,012 | 13 | 37 | 418 | 394 |
| | T statistic | 0.386 | −1.366 | −0.446 | −0.774 | 1.125 |
| | p-value | 0.700 | 0.179 | 0.657 | 0.442 | 0.262 |
| 400 (3) | Avg | 1,310 | 12 | 32 | 331 | 418 |
| | Std | 961 | 8 | 14 | 217 | 256 |
| | Cv | 0.73 | 0.67 | 0.45 | 0.66 | 0.61 |
| | Max | 3,042 | 33 | 63 | 910 | 963 |
| | Min | 13 | 0 | 8 | 75 | 58 |
| | Median | 1,202 | 11 | 32 | 307 | 395 |
| | T statistic | 0.239 | 0.812 | 3.393 | 1.998 | 1.821 |
| | p-value | 0.812 | 0.418 | 0.001 | 0.048 | 0.071 |
| 300 (2) | Avg | 1,371 | 21 | 55 | 688 | 535 |
| | Std | 1,219 | 19 | 37 | 941 | 419 |
| | Cv | 0.89 | 0.91 | 0.68 | 1.37 | 0.78 |
| | Max | 4,696 | 86 | 205 | 5,495 | 2,324 |
| | Min | 93 | 1 | 13 | 79 | 83 |
| | Median | 1,025 | 17 | 46 | 473 | 480 |
| | T statistic | −0.004 | −0.062 | −1.464 | −1.262 | 0.405 |
| | p-value | 0.997 | 0.951 | 0.150 | 0.214 | 0.686 |
| 100 (1) | Avg | 1,296 | 20 | 54 | 677 | 497 |
| | Std | 1,189 | 20 | 37 | 944 | 408 |
| | Cv | 0.92 | 0.96 | 0.70 | 1.39 | 0.82 |
| | Max | 4,696 | 86 | 205 | 5,495 | 2,324 |
| | Min | 93 | 1 | 14 | 101 | 94 |
| | Median | 904 | 15 | 44 | 457 | 432 |
| | T statistic | 0.253 | 0.117 | −1.341 | −1.199 | 0.766 |
| | p-value | 0.801 | 0.907 | 0.186 | 0.237 | 0.446 |

Figure 24:
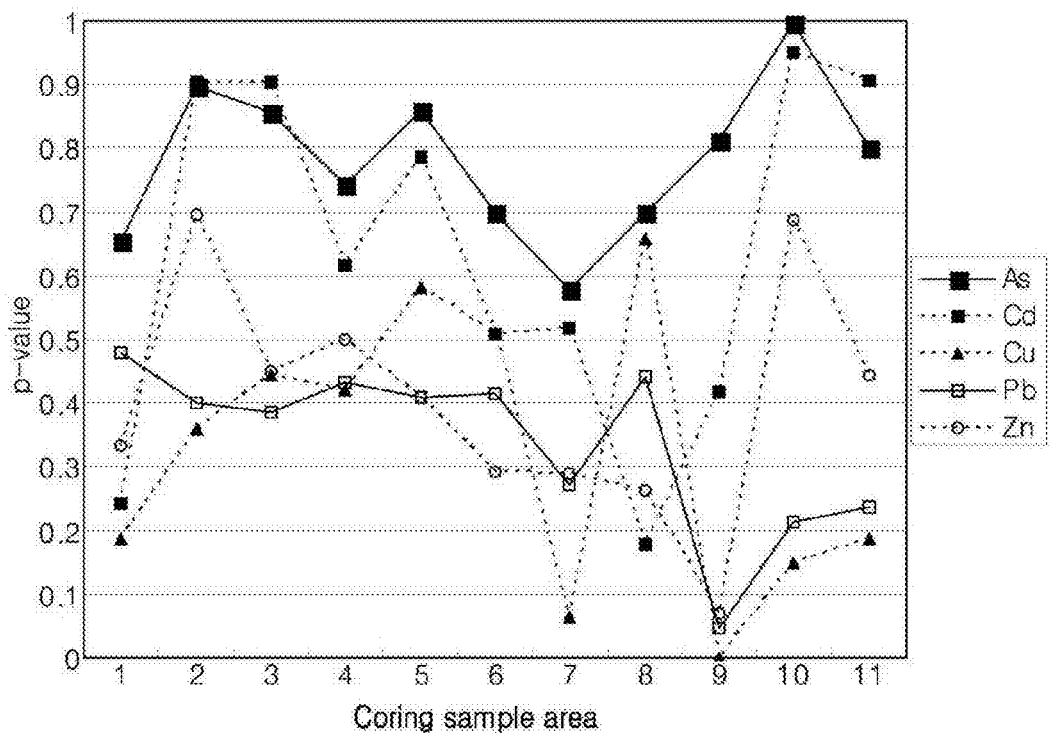
FIG. 24 is a graph showing the p-value as a function of the coring sample area.

FIG. 24 is a graph showing the p-value as a function of the coring sample area.

As shown in FIG. 24, the p-value of Cu and Pb was lower than 0.05 in the area of 400 m² (Cu: 0.001 and Pb: 0.048). Thus, it is necessary to collect the coring samples from the area of at least 500 m² to ensure the representativeness of the samples.

Figure 25:
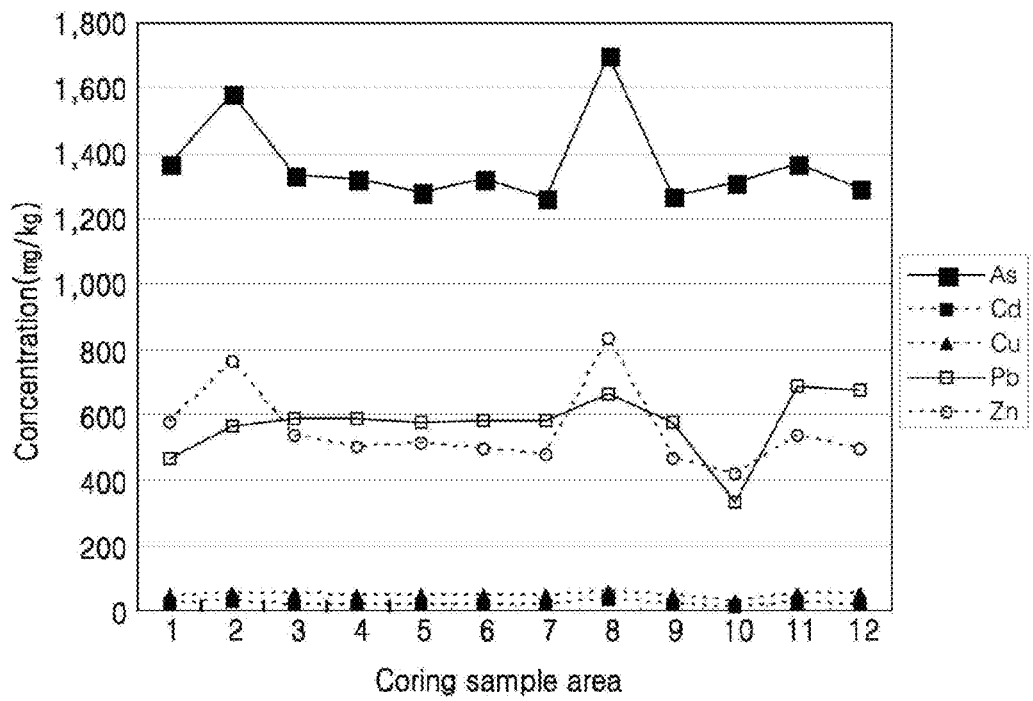
FIG. 25 is a graph showing concentration of trace elements as a function of the coring sample area.

FIG. 25 is a graph showing the concentration of the trace elements as a function of the coring sample area.

As shown in FIG. 25, the average concentration of the trace elements was constant regardless of the size of the sampling area. Exceptionally, As, Pb and Zn represented very high or very low average concentration caused by the non-uniformity of the sample.

Figure 26:
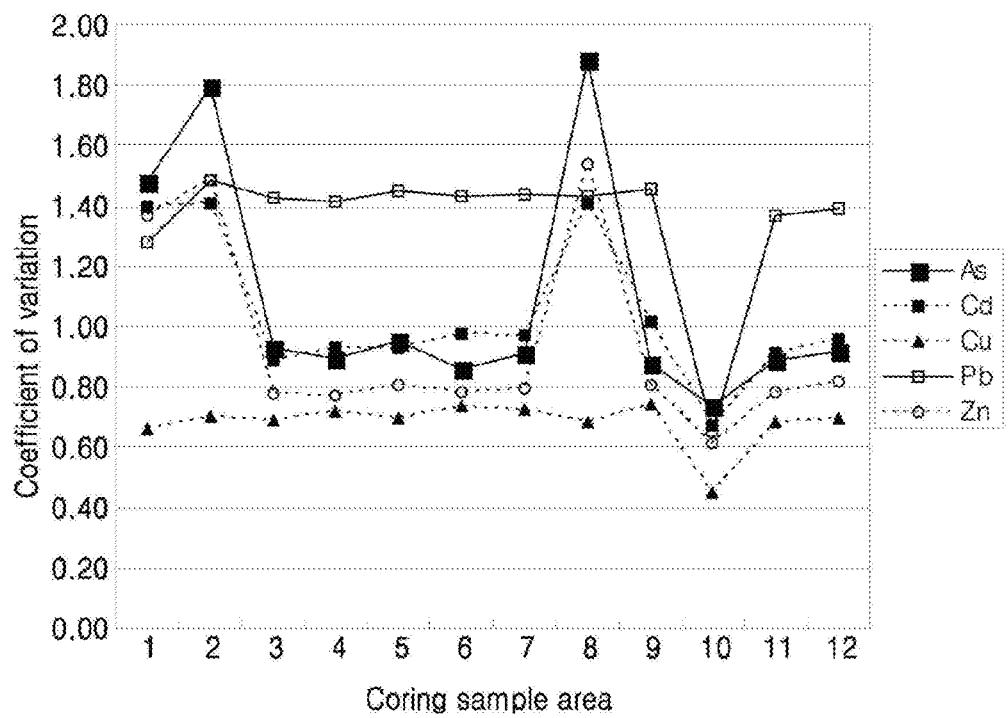
FIG. 26 is a graph showing the coefficient of variation as a function of the coring sample area.

FIG. 26 is a graph showing the coefficient of variation as a function of the coring sample area.

As shown in FIG. 26, the coefficient of variation as a function of the coring sample area was very similar to the variation of the average concentration. This result reflects that the standard deviation was increased as the total concentration of the trace elements was increased. In addition, this result indicates the non-uniformity of the samples provided in the tailing heap.

(E) DISCUSSION AND CONCLUSION

The conclusion of the research for establishing the standardization of the method for collecting samples having the representativeness from the tailings is as follows. When the horizontal samples were collected at the regular interval of 30M (meters) or less, the average concentration of the trace elements in the tailings was identical to the average concentration in all samples (that is, the samples collected at the regular interval of 5M (meters)). However, when the horizontal samples were collected at the regular interval of 35M (meters) or above, the average concentration of Cu represented the significant difference (p-value: 0.039). Thus, it is necessary to collect the horizontal samples at the regular interval of at least 30M (meters) to ensure the representativeness for the tailings (See, table 9).

Meanwhile, according to the vertical (depth) sampling method, the average concentration of the trace elements had the representativeness for the tailings when the depth was at least 2.0M (meters) and the sample number was at least 4. In detail, the concentration of Cu represented difference with respect to the average concentration in all samples when the depth was 1.5M (meters) (p-value: 0.029). In addition, the concentration of Cu represented difference with respect to the average concentration in all tailings when the sample number was 3 (p-value: 0.020).

Although a preferred embodiment of the present invention has been described for illustrative purposes, those skilled in the art will appreciate that various modifications, additions and substitutions are possible, without departing from the scope and spirit of the invention as disclosed in the accompanying claims.

Although the present invention has been described by making reference to the embodiments and accompanying drawings, it should be understood that the present invention is not limited to the embodiments but includes all modifications, equivalents and alternatives. Accordingly, those skilled in the art should understand the spirit and scope of the present invention as defined in the following claims. In addition, those skilled in the art should understand that the equivalents and the modifications belong to the scope of the spirit of the present invention.

What is claimed is:

1. A method for verifying representativeness of samples collected in a contaminated soil, the method comprising:
    horizontally and vertically collecting the samples from the contaminated soil on a basis of a stratum of the contaminated soil at a predetermined sampling interval;
    measuring a total concentration of trace elements by using a chemical analysis instrument to analyze the collected samples according to the sampling interval, wherein the total concentration of the trace elements is measured through a pretreatment by using aqua regia and a chemical analysis by using an inductively coupled plasma-atomic emission spectroscopy (ICP-AES) instrument as the chemical analysis instrument; and
    determining horizontal and vertical sampling intervals and a sample number based on a statistical analysis result for the total concentration of the trace elements,
    wherein the horizontal collecting of the samples comprises regularly setting the sampling intervals and gradually widening the sampling intervals in a horizontal direction by a predetermined distance;
    wherein the vertical collecting of the samples comprises regularly setting the sampling intervals and gradually widening the sampling intervals in a vertical direction by a predetermined distance, and
    wherein the horizontal sampling interval is regularly set within 30 m, the vertical sampling interval is set to at least 2 m, the sample number of vertically collected samples is at least 4, and an area for vertically collecting the samples is at least 500 m².

2. The method of claim 1, wherein the statistical analysis for the total concentration of the trace elements comprises:
    sub-dividing all samples into sub-groups; and
    comparing whether an average concentration of trace elements in each sub-group is identical to an average concentration of trace elements in all samples.

TABLE 9

Sampling locations of tailings from Samgwang mine

| 1-1 | 2-1 | 3-1 | 4-1 | 5-1 | 6-1 | 7-1 | 8-1 | 9-1 | 10-1 | 11-1 | 12-1 | 13-1 | 14-1 | 15-1 | 16-1 | 17-1 | 18-1 | 19-1 | 20-1 |
|---|---|---|---|---|---|---|---|---|---|---|---|---|---|---|---|---|---|---|---|
| 1-2 | 2-2 | 3-2 | 4-2 | 5-2 | 6-2 | 7-2 | 8-2 | 9-2 | 10-2 | 11-2 | 12-2 | 13-2 | 14-2 | 15-2 | 16-2 | 17-2 | 18-2 | 19-2 | 20-2 |
| 1-3 | 2-3 | 3-3 | 4-3 | 5-3 | 6-3 | 7-3 | 8-3 | 9-3 | 10-3 | 11-3 | 12-3 | 13-3 | 14-3 | 15-3 | 16-3 | 17-3 | 18-3 | 19-3 | 20-3 |
| 1-4 | 2-4 | 3-4 | 4-4 | 5-4 | 6-4 | 7-4 | 8-4 | 9-4 | 10-4 | 11-4 | 12-4 | 13-4 | 14-4 | 15-4 | 16-4 | 17-4 | 18-4 | 19-4 | 20-4 |
| 1-5 | 2-5 | 3-5 | 4-5 | 5-5 | 6-5 | 7-5 | 8-5 | 9-5 | 10-5 | 11-5 | 12-5 | 13-5 | 14-5 | 15-5 | 16-5 | 17-5 | 18-5 | 19-5 | 20-5 |
| 1-6 | 2-6 | 3-6 | 4-6 | 5-6 | 6-6 | 7-6 | 8-6 | 9-6 | 10-6 | 11-6 | 12-6 | 13-6 | 14-6 | 15-6 | 16-6 | 17-6 | 18-6 | 19-6 | 20-6 |
| 1-7 | 2-7 | 3-7 | 4-7 | 5-7 | 6-7 | 7-7 | 8-7 | 9-7 | 10-7 | 11-7 | 12-7 | 13-7 | 14-7 | 15-7 | 16-7 | 17-7 | 18-7 | 19-7 | 20-7 |
| 1-8 | 2-8 | 3-8 | 4-8 | 5-8 | 6-8 | 7-8 | 8-8 | 9-8 | 10-8 | 11-8 | 12-8 | 13-8 | 14-8 | 15-8 | 16-8 | 17-8 | 18-8 | 19-8 | 20-8 |
| 1-9 | 2-9 | 3-9 | 4-9 | 5-9 | 6-9 | 7-9 | 8-9 | 9-9 | 10-9 | 11-9 | 12-9 | 13-9 | 14-9 | 15-9 | 16-9 | 17-9 | 18-9 | 19-9 | 20-9 |

3. The method of claim 2, wherein the sub-groups include samples selected by taking the sampling interval into consideration in a case of horizontally collected samples, and include samples selected by taking at least one of a sampling location, an area, a depth and a sample number into consideration in a case of vertically collected samples.

4. The method of claim 1, wherein the sampling interval is determined by taking a compression rate of each sample according to the depth into consideration in the case of the vertically collected samples.

5. The method of claim 1, further comprising;
making a contour map based on the statistical analysis result for the total concentration of the trace elements in horizontally collected samples; and
confirming uniformity of the concentration of each trace element by using the contour map.

6. The method of claim 1, further comprising;
confirming uniformity of horizontally collected samples through a $\chi^2$ test, wherein $\chi^2$ test=$\Sigma\{(O-E)^2/E\}$, O is an observation value (analysis value) and E is an expectation value (average value).

7. The method of claim 1, further comprising;
confirming a variance of horizontally collected samples by using a box plot.

8. The method of claim 1, wherein the samples are collected in a single mine.

* * * * *